(12) United States Patent
Erikson et al.

(10) Patent No.: US 6,358,738 B1
(45) Date of Patent: Mar. 19, 2002

(54) POLO BOX THERAPEUTIC COMPOSITIONS, METHODS, AND USES THEREFOR

(75) Inventors: Raymond L. Erikson, Cambridge, MA (US); Kyung S. Lee, Potomac, MD (US)

(73) Assignee: The President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/311,311

(22) Filed: May 13, 1999

Related U.S. Application Data

(60) Provisional application No. 60/085,296, filed on May 13, 1998.

(51) Int. Cl.⁷ .......................... C12N 5/00; A61K 38/51; A61K 38/16
(52) U.S. Cl. ...................... 435/375; 435/377; 424/94.5; 514/12
(58) Field of Search .......................... 424/94.5; 514/12; 435/375

(56) References Cited

PUBLICATIONS

Bohm, H. et al., 1991, *Biomed.Biochim. Acta* 50:1193–1203.
Llamazares, S. et al., 1991, *Genes & Development* 5:2153–2165.
Crews, C. et al., 1992, *Science* 258:478–480.
Simmons, D. et al., 1992, *Mol. Cell. Biol.* 12:4164–4169.
Clay, F. et al., 1993, *Proc. Natl. Acad. Sci. USA* 90:4882–4886.
Vojtek, A. et al., 1993, *Cell* 74:2–5–214.
Lake, R. et al., 1993, *Mol. Cell. Biol.* 13:7793–7801.
Kitada, K. et al., 1993, *Mol. Cell. Biol.* 13:4445–4457.
Fode, C. et al., 1994, *Proc. Natl. Acad. Sci. USA* 91:6388–6392.
Gonen, H. et al., 1994, *Proc. Natl. Acad. Sci. USA* 91: 7648–7652.
Hamanaka, R. et al., 1994, *Cell Growth Different.* 5:249–257.
Ohkura, H. et al., 1995, *Genes & Development* 9:1059–1073.
Donohue, P. et al. 1995, *J Biol Chem.* 270:10351–10357.
Coux, O. et al., 1996, *Ann. Rev. Biochem.* 65:801–847.
Kumagai, A. et al., 1996, *Science* 273:1377–1380.
Lane, H. et al., 1996, *J. Cell Biol.* 135:1701–1713.
Lee, K. et al., 1997, *Mol. Cell. Biol.* 17:3408–3417.
Liang, P. et al., 1997, *J.Cell Sci.* 110:1431–1440.
Toczyski, D. et al., 1997, *Cell* 90:1097–1106.
Barr, F. et al., 1998, *EMBO J.* 17:3258–3268.
Lowe, M. et al., 1998, *Cell* 95:783–793.
Shirayama, M. et al., 1998, *EMBO J.* 17:1336–1349.
Descombes P. et al., 1998, *EMBO J.* 17:1328–1335.

*Primary Examiner*—Elizabeth Slobodyansky
(74) *Attorney, Agent, or Firm*—Bromberg & Sunstein LLP

(57) ABSTRACT

The amino acid sequence of a polo box is provided based on residue-by-residue mutation and analysis of phenotype. Additional polo boxes in the polo kinase protein located between the first polo box and the carboxy terminal are provided. Compositions and methods are provided for obtaining inhibitors of polo box function, for use as therapeutics for treatment of cancer, infection a fungi, protozoans, and helminths, for arthropod infestation of a subject, and for treatment of tumors.

9 Claims, 13 Drawing Sheets

```
              ***         218 222  *        ***
Mek1  CDFGVSGQL--IDSMANSFVGTRSYMSPE 206 210
Plk   GDFGLATKVEYEGERKKTLCGTPNYIAPE
Plx1  GDFGLATKVEYDGERKKTLCGTPNYIAPE
polo  GDFGLATRIEYEGERKKTLCGTANYIAPE
Plo1  GDFGLAALLMDDERKMTICGTPNYIAPE
Cdc5  GDFGLAAVLANESRKYTICGTPNYIAPE
Sak   ADFGLATQLNMPHEKHYTLCGTPNYISPE
Snk   GDFGLAARLEPLHRRRTICGTPNYLSPE
Fnk   GDFGLAARLEPPQRKKTICGTPNYVAPE
Prk   GDFGLAARLEPPQRKKTICGTPNYVAPE
```

FIGURE 1

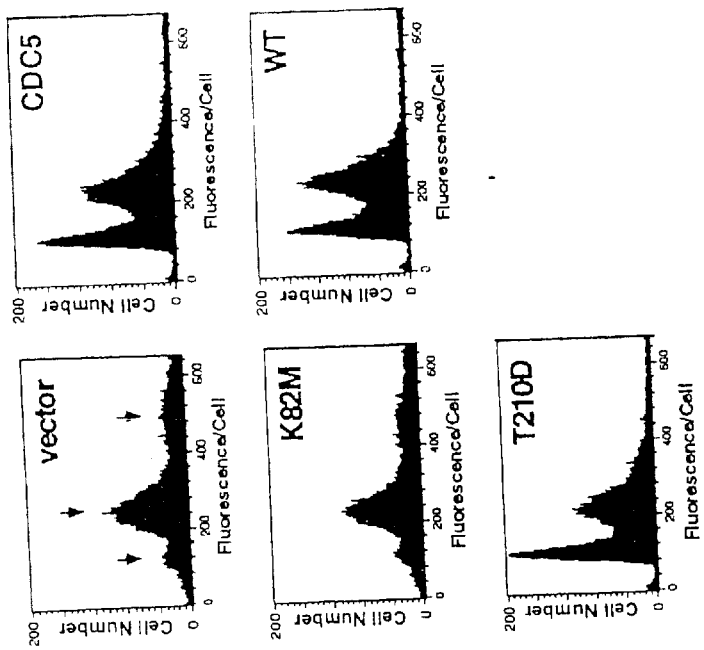
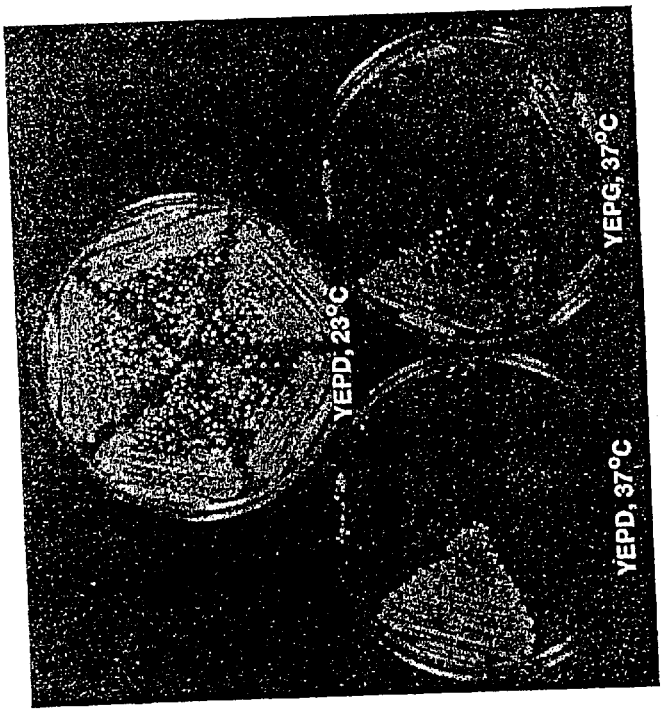
FIGURE 3

```
                          Polo-box
Plk       VRQEEAEDPA CIPIFWVSKW VDYSDKYGLG YQLCDNSVGV LENDSTRLIL YNDGDSLQYI
polo      NLGDENTDPA AQPLFWISKW VDYSDKYGFG YQLCDEGIGV MFNDTTKLIL LPNQINVHFI
Plo1      THALTSEDAD SEPVLFITKW VDYSNKYGLG YQLSDESVGV HFNDDTSLLF SADEEVVEYA
Cdc5      GLPKSRLPKI KHPMI.VTKW VDYSNKHGFS YQLSTEDIGV LFNNGTTVLR LADAEEFWYI
Consensus ..........D.. ..P......KW VDYS.KYG.G YQL.DE..GV .FND.T.L.. ..D.....YI Plk       ....ERDGTE SYLTVSSHPN SLMKKITLLN YFRNYMSEHL LKA..GRNIT PREGDELARL
polo      ....DKDGKE TYMTTTDYCK SLDKKMKLLS YFKKRYMIEHL VKA..GANNV NIESDQISRM
Plo1      LHPKDTEIKP YIYPASKVPE SIRSKLQLLK HFKSYMGQNL SKAVQDESFE KPKNSTSNTM
Cdc5      SYDDREGWVA SHYLLSEKPR ELSRHLEVVD FFAKYMKANL SRVSTFGREE YHKDD.....
Consensus ..........  ....S..P. SL..K..LL. F.YM...L ..KA....... .....D....
                                          PB2

Plk       PYLRTWFRTR SAIILHLSNG TVQINFFQDH TKLILCPLMA AVTYINEKRD FQTYRLSLLE
polo      PHLHSWFRTT CAVVMHLTNG SVQLN.FSDH MKLILCPRMS AITYMDQEKN FRTYRFSTIV
Plo1      LFMQHYLRTR QAIMFRLSNG IFQFN.FLDH RKVVISSTAR KIIVLDKER. .ERVELPLQE
Cdc5      VFLRRYTRYK PFVMFELSDG TFQFN.FKDH HKMAISDGGK LVTYISPSHE STTYPLVEVL
Consensus ..L....RT. A....LSNG ..O.N.F.DH ..K....... ..TY...... ..TY.L...
                                PB3

Plk       EYGCCKEL.A SRLRYARTMV DKLLSSRSAS NRLKAS
polo      ENGVSKDL.Y QKIRYAQEKL RKMLEKMFT~ ~~~~~~
Plo1      ASAFSEDL.R SRLKYIRETL ESWASKMEVS ~~~~~~
Cdc5      KYGEIPGYPE SNFREKLTLI KEGLKQKSTI VTVD~~
Consensus ..G.....L.. S..RY...... .....L..... ......
```

FIGURE 10

[a) *GRASP65 (Golgi Re-Assembly Stacking Protein).*

Figure    Sequence of GRASP65.

```
  1 MGLGASSEOP AGGEGFHLHG VQENSPAQQA GLEPYFDFII TIGHSRLNKE NDTLKALLKA
 61 NVEKPVKLEV FNMKTMRVRE VEVVPSNMWG GOGLLGASVR FCSERRASEH VWHVLDVEPS
121 SPAALAGLRP YTDYIVGSDQ ILQESEDEFT LIESHEGKPL KLMVYNSESD SCREVTVTPN
181 AAWGGEGSLG CGIGYGYLHR IPTQPSSQYK KPPSASSPGT PAKTPQPNAF PLGAPPWPI
241 PQDSSGPELG SRQSDYMEAL PQVPGGFMEE QLPGPGSPGH GTADYGGCLH SMEIPLQPPP
301 PVQRVMDPGF LDVSGM*SLLD* SNNTSVCPSL SSS*SLLT*PTA VSALGPEDIG SSTSSHERGG
361 EATWSGSEFE ISFPDSPGSQ AQVDHLPRLT LPDGLTSAAS PEQGLSAELL EAQTEEPHTR
421 SACIAWHKLR GHPANSRLPH IQSLGCVKAP GDIWCSLAVY LSSCSLYRGM GFATVHMYSW
481 IERNRTLEQC PASIEAGDGS NVSVKHWHLP GRERLQARHN VHMKMGWGTR GCVHKRPHWY
541 RGAPRIPMPF LILILTLDER SSILGHLISR MEDSGPFRGT CLC
```

XXX    Sequence of GRASP65 in cDNA clone detected with Plk (1-400) and Plk (323-499) bait.

<u>XXX</u>    Region of GRASP65 reported to interact with GM130.

*XXX*    Putative Plk phosphorylation sites in GRASP 65, *SLL*.

FIGURE 12

Sequence of CCT-ε

```
  1  MASVGTLAFD EYGRPFLIIK DQDRKSRLMG LEALKSHIMA AKAVANTMRT
 51  SLGPNGLDKM MVDKDGDVTI TNDGATILSM MDVDHQIAKL MVELSKSQDD
101  EIGDGTTGVV VLAGALLEEA EQLLDRGIHP IRIADGYEQA ARIAIQHLDK
151  ISDKVLVDIN NPEPLIQTAK TTLGSKVINS CHRQMAEIAV NAVLTVADME
201  RRDVDFELIK VEGKVGGRLE DTKLIKGVIV DKDFSHPQMP KKVVDAKIAI
251  LTCPFEPPKP KTKHKLDVMS VEDYKALQKY EKEKFEEMIK QIKETGANLA
301  ICQWGFDDEA NHLLLQNGLP AVRWVGGPEI ELIAIATGGR IVPRFSELTS
351  EKLGFAGVVQ EISFGTTKDK MLVIEKCKNS RAVTIFIRGG NKMIIEEAKR
401  SLHDALCVIR NLIRDNRVVY GGGAAEISCA LAVSQEADKC PTLEQYAMRA
451  FADALEVIPM ALSENSGMNP IQTMTEVRAR QVKESNPALG IDCLHKGSND
501  MQYQHVIETL IGKKQQISLA TQMVRMILKI DDIRKPGESE E
```

<u>XXX</u>   Sequence of CCT-ε in cDNA clone detected with Plk (323-499) bait.

POLO BOX THERAPEUTIC COMPOSITIONS, METHODS, AND USES THEREFOR

RELATED APPLICATION

This application claims priority from provisional application 60/085,296 filed May 13, 1998, which is hereby incorporated by reference herein.

GOVERNMENT FUNDING

This invention was made in part with government support under grant CA42580 awarded by the National Institutes of Health. The government has certain rights in the invention.

TECHNICAL FIELD

The present invention relates to the structure and function of the polo-box of the mitotic protein polo kinase gene, to proteins that bind to the polo box and their encoding genes, and particularly to compositions and methods for modulation of polo box function and regulation of mitotic processes for treatment of a subject having unwanted eukaryotic cells such as cancer, fungal pathogens, pathogenic protozoans, helminths, and arthropod cells.

BACKGROUND OF THE INVENTION

Polo kinases are found in diverse eukaryotic organisms, as represented by mammalian Plk, amphibial *Xenopus laevis* Plx1, and others shown in FIG. 1, and share a region of sequence homology in the carboxy terminal (C-terminal) non-catalytic domain termed the polo-box (Clay, F. J. et al., 1993, *Proc. Natl. Acad. Sci. USA* 90: 4882–4886). Genetic and biochemical analyses show that polo kinases affect diverse cellular events during M phase such as centrosome maturation (Lane, H. A. et al., 1996, *J. Cell Biol*, 135: 1701–1713) and bipolar spindle formation (Llamazares, S., et al., 1991, *Genes & Development*, 5: 2153–2165; Ohkura, H., et al., 1995, *Genes & Development*, 9: 1059–1073. Polo kinases appear to affect steps in the transition from G2 to M ($G_2$/M) phase, such as activation of Cdc2 through Cdc25C phosphatase (Kumagai, A., et al., 1996, *Science*, 273: 1377–1380), DNA damage checkpoint adaptation (Toczyski, D. P. et al., 1997, *Cell*, 90: 1097–1106), and the anaphase-promoting complex (Shirayama, M. et al., 1998, *EMBO J*, 17: 1336–1349); Descombes et al., 1998, *EMBO J*, 17: 1328–1335). Expression of Plo1 or Plk has been shown to induce cytokinesis-associated septation structures (Ohkura, H., et al., 1995, *Genes & Development*, 9: 1059–1073).

The exact structure and the function of the conserved sequence polo box in the non-catalytic domain polo-box are undefined. Regulatory sites in other regions of the gene have not been defined. This no information on cellular elements such as proteins that interact with the polo kinase. Regulation of polo kinase activity and the role of the polo kinase protein in regulation of events of mitosis are not understood.

SUMMARY OF THE INVENTION

An embodiment of the invention is a composition having sufficient affinity for a polo-box of a polo kinase so as to inhibit localization of a polo kinase in a cell. The composition can be a peptide or a peptide analog, for example, a peptide is selected from the group consisting of an amino acid sequence from a tubulin, an actin, a chaperonin, a Golgi protein, and a translationally controlled tumor protein, or it can comprise all or a portion of a carboxy terminal of a polo kinase. Further, the composition having sufficient affinity for a polo-box of a polo kinase can be a peptidomimetic.

An embodiment of the invention is a composition which is a peptide amino acid sequence comprising all or a portion of an amino acid consensus sequence in the carboxy terminal of polo kinase proteins of eukaryotic organisms, the consensus sequence being located between and not including the polo box PB1 (SEQ ID NO: 1) and the carboxy terminal. The composition of this embodiment is selected from the group consisting of amino acid sequences comprising all or a portion of:

$NH_2$-ser-X-X-pro-X-ser-leu-X-X-lys-X-X-leu-leu-X-X-phe-X-X-tyr-met-X-X-X-leu-X-lys-ala-COOH (PB2; SEQ ID NO:6), and $NH_2$-leu-X-X-X-X-arg-thr-X-X-ala-X-X-X-X-leu-ser-asn-gly-X-X-gln-X-asn-X-phe-X-asp-his-X-lys-COOH (PB3; SEQ ID NO:7), wherein X in a position denotes an unspecified amino acid residue. Further, the composition can be a polynucleotide selected from the group consisting of: a polynucleotide encoding an amino acid sequence according PB2 and PB3 (SEQ ID Nos:6 and 7), and a polynucleotide complementary to such a polynucleotide. The composition which is a peptide of amino acid sequence according to these polo box consensus sequences, can be obtained from a target cell selected from the group of cells consisting of a fungus, a protozoan, an arthropod, a helminth, and a tumor cell of a mammal, so that in the amino acid sequence the amino acid residues denoted X are obtained from the amino acid sequence of a polo kinase in a cell which is an unwanted cell in a subject.

Another embodiment of the invention is a method of inhibiting growth of an unwanted cell in a subject by introducing into the cell a polo-box binding inhibitor, for example, a peptide or peptide analog comprising an amino acid sequence of a polo kinase, for example, the amino acid sequence from the carboxy terminal of the polo kinase. In this embodiment of the invention, the unwanted cell in the subject can be a cancer cell, for example, a cancer of a lung, a breast, a uterus, an ovary, a cervix, an epithelium, a brain, a retina, a prostate, and a throat. Further, the unwanted cell in the subject can be a cell of a fungus, a protozoan, an arthropod, and a helminth.

Another embodiment of the invention is a method of inhibiting cell division of an unwanted cell by modulation of a function of a polo kinase in a cell, for example, modulation of localization of a polo kinase during a mitotic phase of a cell.

An embodiment of the invention is a method for screening for an agent that modulates activity of a polo kinase comprising: culturing under permissive and restrictive growth conditions a cell, the cell having a conditional lethal endogenous chromosomal polo kinase gene complemented by a recombinant vector encoding a regulatable polo kinase gene such that growth of the cell at the restrictive condition is dependent on expressing the regulatable gene; inducing expression of the regulatable polo kinase gene; and exposing a portion of the culture of the cell to a candidate agent under the permissive and the restrictive growth condition, so that inhibition of growth of the cell in the presence but not the absence of the candidate inhibitor at the restrictive growth condition is an indication that the candidate inhibitor is an agent that modulates the activity of the polo kinase. In this embodiment, the polo kinase can be one that is selected from the group of consisting of a polo kinase from a fungus, a protozoan, an arthropod, a helminth, and a tumor cell. This method can comprise an additional step of testing the candidate inhibitor in a pharmaceutically acceptable carrier for appropriate dose in preclinical testing with an animal model system, for example, an animal infected with a fungus. The fungal infection can be selected from the group consisting of aspergillosis, candidiasis, a *Lichen planus* infection, and athlete's foot.

Another embodiment of the invention is a method for obtaining a DNA sequence encoding a peptide that binds to a polo box peptide, comprising: constructing a two-hybrid system wherein the bait is a peptide having an amino acid sequence comprising a polo box and the prey is is a cDNA library, the binding of the two hybrid proteins of the bait and the potential prey causing a change in a selectible phenotype of the cell; transforming a population of the cells with the constructed two-hybrid vector carry the library of donor DNA sequences; growing the cells under conditions that induce expression of the two-hybrid fusion genes and the appearance of the selectible phenotype in cells carrying a DNA sequence encoding a potential prey peptide that binds to a polo box peptide; and selecting cells expressing the selectible phenotype to isolate a cell clone carrying a DNA sequence from the library, such that the translation product of the cloned DNA binds to the polo box of the polo kinase. This method can have the additional step of sequencing the cloned DNA. Further, this method can have the additional step of isolating the gene from the donor organism comprising the cloned DNA encoding the prey. From this method that is an embodiment of the invention can be cloned a cortical actin, a septin, a tubulin, a cytoplasmic chaperonin complex protein, a Golgi protein, and a translationally controlled tumor protein, for example, a peptide of a protein selected from the group consisting of: a polo kinase C-terminal, a Grasp 65 (SEQ ID No:24), a chaperonin-containing-TCP (CCT-ε), and a translationally controlled tumor protein p23 (TCTP/p23) (SEQ ID No:27). Further, this method can comprise an additional step of determining an effective dose of the modulator for a subject having an unwanted cell which is selected from the group of cells consisting of a human cancer cell, an arthropod cell, and a fungal cell. By use of the method of inhibiting growth of an unwanted cell in a subject, one can administer to the subject an effective dose of the modulator obtained, in a pharmaceutically acceptable carrier.

An embodiment of the invention provides a method of developing an organism-specific polo box binding inhibitor, comprising: providing a sequence of a polo kinase from the organism; identifying the organism's polo boxes in the polo kinase from the organism by aligning the sequence of the polo kinase from the organism with each of PB1 (SEQ ID NO:1), PB2 (SEQ ID NO:6) and PB3 (SEQ ID NO:7) and using all or a portion of the organism's polo boxes to develope a polo box binding inhibitor.

BRIEF DESCRIPTION OF THE DRAWINGS

FIG. 1 shows an amino acid sequence alignment among polo subfamily member amino acid sequenced (SEQ ID NOS 8–17).

FIG. 3 shows complementation of the mutant phenotype of *Saccharomyces cerevisiae* cdc5-1 cell growth and cell cycle defects by ectopic expression of Plk. Panel A shows growth of colonies of cdc5-1 mutant strain (KKY921-2B) transformed with YCplac111-GAL1-HA-PLK mutations or with YCplac111-CDC5, selected on synthetic minimal medium lacking leucine. Strains clockwise from the top of the plate are: Vector control: HA-PlkK82M, HA-Plk, HA-PlkT210D, and CDC5. CDC5 is expressed under its own promoter and complements cdc5-1 under all conditions shown. Plk constructs can function when induced by galactose in the YEPG medium, but not in glucose medium (YEPD). Panel B shows flow cytometric analyses of the cdc5-1 cells expressing Plk mutations. Expression of Plk WT or T210D restores the cdc5-1 cell division defect to an extent similar to that of endogenous CDC5. CDC5 gene: YCplac111-CDC5; vector control: YCplac111-GAL1; K82M gene: Ycplac111-GAL1-HA-PlkK82M; WT gene: YCplac111-GAL1-HA-Plk; T210D gene: YCplac111-GAL1-HA-PlkT210D.

FIG. 10 shows the sequence alignment of the C-termini of four M phase-specific polo kinase (SEQ ID NOs:20–23); and the consensus observed herein for each of the original polo box (Clay, F. et al., 1993, *Proc. Natl. Acad, Sci. USA* 90:4882–48860) designated here PB1 (SEQ ID NO:1), and the embodiments of the invention that are the additional downstream polo boxes, PB2 (SEQ ID NO:6), and PB3 (SEQ ID NO:7).

FIG. 12 shows the full sequence of GRASP65 (SEQ ID No:24), with underlined residues indicating the amino acid sequence of clones obtained from the two-hybrid system with Plk 1–400 (SEQ ID No:26) and Plk 323–499 (SEQ ID No:26) as bait.

FIG. 13 shows the full amino acid sequence of CCT-ε (SEQ ID No:25), including the underlined portion of the sequence isolated as prey using mammalian Plk residues 323–499 (SEQ ID No:26) as bait in the two-hybrid system (Vojtek, A. et al., 1993, *Cell* 74:205–214).

DETAILED DESCRIPTION OF THE EMBODIMENTS

Figure 2:
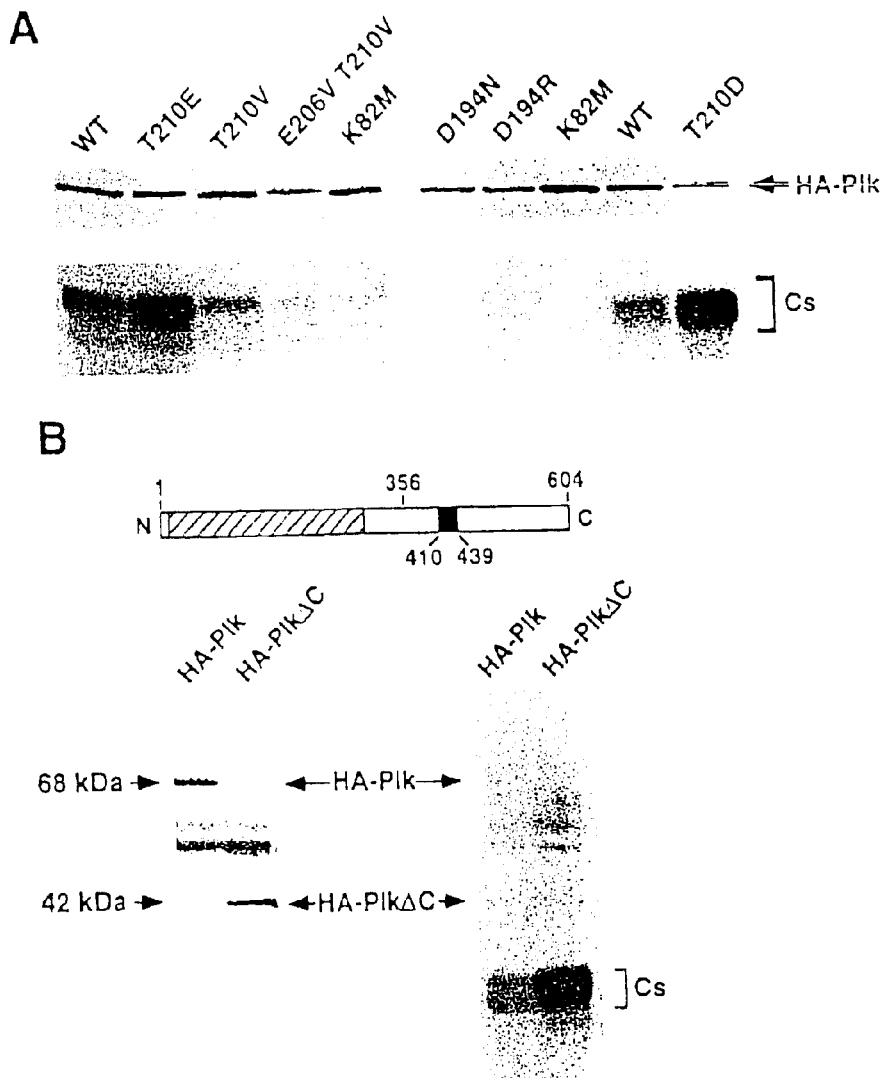
FIG. 2 shows in vitro kinase activity of Plk mutants expressed in insect cells. Hemagglutinin (HA)-tagged HA-Plk proteins were immunoprecipitated from Sf9 cells expressing various recombinant HA-Plk mutants, the mutant in each lane indicated using the letter of the original amino acid followed by the residue number and the substituted amino acid in the mutant; immunoprecipitated proteins were subjected to kinase assays using casein as substrate. Panel A: the upper gel shows the quantity of HA-Plk immunoprecipitated with anti-HA and the lower blot shows mutant proteins immunoprecipitated with anti-Plk antibody. Panel B shows casein phosphorylation activities by wild-type (WT) HA-Plk and its C-terminal deletion mutant (PlkΔC).

The ability of small molecules to interact with protein targets can be used to identify potential new drugs that have specific therapeutic effects in disease states. A drug screen can identify agonists and antagonists that interfere or compete with the binding of molecules in the cell, such as other protein molecules, for these targets. Drug development programs require a continuing supply of novel cell protein targets to serve as the basis of screening systems for identification of drug candidates. Sophisticated cell-based drug screens provide genetically marked strains of cells, which respond to drug candidate chemicals in predictable ways to help identify drugs that bind to proteins and interfere with normal protein function, such as the ability to bind to a second protein and effect a regulatory function.

Many biochemical features of eukaryotic pathogens and parasites, including fungi, protozoans, helminth worms, and arthropods, are difficult to distinguish from those of human and other mammalian host subjects. One feature that eukaryotic pathogens share with each other and with unwanted host cells such as tumor cells, and that differs from the normal cells of human and mammalian hosts, is constant and rapid cell growth and division, with continuous passage of cells through mitosis. For example, growth and development of each of the cells of tumors, pathogenic fungi, and eggs of head lice require constant and rapid mitotic events. In contrast, few normal mammalian cells, other than hematopoietic or gastric epithelial cells, are actively dividing. At a given time, only a few percent of mammalian cells are engaged in mitosis. For this reason, many classical anti-cancer and anti-viral chemotherapeutic agents are inhibitors of DNA synthesis. While these agents are toxic to the host subject, they can differentially affect tumor and virus replication to provide a therapeutic benefit.

The eukaryotic cell cycle

Following mitosis (M phase) and cytokinesis (cell division), a eukaryotic cell enters the G1 phase during which DNA metabolism is relatively quiescent. DNA is synthesized during the subsequent S phase, which is followed by G2 phase during which errors of DNA synthesis are corrected and DNA is repaired, prior to entry into M phase. Transitions from one phase into another are found to be generally tightly regulated. Much information on this subject comes from studies of yeast cell division cycle (cdc) mutants, which exhibit the lethal phenotype of cell cycle arrest at the non-permissive temperature.

The M phase is characterized by major internal cellular changes, including breakdown of the nuclear membrane and the Golgi apparatus, condensation of heterochromatin into chromosomes, the appearance in the cell of spindle fibers and centrioles, and the lining up of chromosomes at the center of the spindle at the metaphase plate. After these changes, the remaining steps of mitosis and cytokinesis are rapidly achieved, resulting in the partition of the genetic material into two daughter cells (the asymmetric products in yeast being known as the mother and daughter cell).

FIG. 1 shows an amino acid sequence alignment among polo subfamily protein members; in all the members of polo subfamily, Glu (E206 in Plk) and Thr (T210 in Plk) were found at sites corresponding to Ser218 and Ser222 in Mek1. Sequences of various cDNAs can be found in the following citations: Mek1 (SEQ ID No:8) (Crews, C. M., et al., 1992, *Science* 258:478–480), mammalian Plk (SEQ ID No:9) (Lake, R. J., et al., 1993, *Mol. Cell. Biol.* 13:7793–7801); amphibial *Xenopus laevis* Plx1 (SEQ ID No:9) (Kumagai, A., et al., 1996, *Science* 273:1377–1380); insect *Drosophila melanogaster* polo (SEQ ID No:11) (Llamazares, S., et al., 1991, *Genes & Development* 5:2153–2165); fungal fission yeast *Schizosaccharomyces pombe* Plo1 (SEQ ID No:12) (Ohkura, H., et al., 1995, *Genes & Development* 9:1059–1073); budding yeast *Saccharomyces cerevisiae* Cdc5 (SEQ ID No:13) (Kitada, K., et al., 1993, *Mol. Cell. Biol.* 13:4445–4457); Sak (SEQ ID No:14) (Fode, C., B. et al., 1994, *Proc. Natl. Acad. Sci. USA* 91:6388–6392); Snk (SEQ ID No:15) (Simmons, D. L., et al., 1992, *Mol. Cell. Biol.* 12:4164–4169); Fnk (SEQ ID No:16) (Donohue, P. J. et al, 1995. *J Biol Chem* 270:10351–10357); and Prk (SEQ ID No:17) (Li, B., et al., 1996, *J Biol. Chem.* 271:19402–19408). Asterisks indicate the conserved residues present in protein kinase subdomains VII and VIII.

The foregoing features of the invention will be more readily understood by reference to the following detailed description, taken with references to the accompanying drawings, in which:

FIG. 1 shows an amino acid sequence alignment among polo subfamily protein members; in all the members of polo subfamily, Glu (E206 in Plk) and Thr (T210 in Plk) were found at sites corresponding to Ser218 and Ser222 in Mek1. Sequences of various cDNAs can be found in the following citations: Mek1 (Crews, C. M., et al., 1992, *Science* 258:478–480), mammalian Plk (Lake, R. J., et al., 1993, *Mol. Cell. Biol.* 13:7793–7801); amphibial *Xenopus laevis* Plx1 (Kumagai, A., et al., 1996, *Science* 273:1377–1380); insect *Drosophila melanogaster* polo (Llamazares, S., et al., 1991, *Genes & Development* 5:2153–2165); fungal fission yeast *Schizosaccharomyces pombe* Plo1 (Ohkura, H., et al., 1995, *Genes & Development* 9:1059–1073); budding yeast *Saccharomyces cerevisiae* Cdc5 (Kitada, K., et al., 1993, *Mol. Cell. Biol.* 13:4445–4457); Sak (Fode, C., B. et al., 1994, *Proc. Natl. Acad. Sci. USA* 91:6388–6392); Snk (Simmons, D. L., et al., 1992, *Mol. Cell. Biol.* 12:4164–4169); Fnk (Donohue, P. J. et al, 1995. *J Biol Chem* 270:10351–10357); and Prk (Li, B., et al., 1996, *J Biol. Chem.* 271:19402–19408). Asterisks indicate the conserved residues present in protein kinase subdomains VII and VIII.

The one-letter and three letter codes (amino acid) used throughout the invention are: A means ala (alanine); C means cys (cysteine); D means asp (aspartic acid); E means glu (glutamic acid); F means phe (phenylalanine); G means gly (glycine); H means his (histidine); I means ile (isoleucine); K means lys (lysine); L means leu (leucine); M means met (methionine); N means asn (asparagine); P means pro (proline); Q means glu (glutamic acid); R means arg (arginine); S means ser (serine); T means thr (threonine); V means val (valine); W means trp (tryptophan); and Y means tyr (tyrosine). Where used, X denotes any amino acid residue at the residue so indicated.

FIG. 2 shows in vitro kinase activity of Plk mutants expressed in Sf9 cells. Hemagglutinin (HA)-fused HA-Plk mutant proteins were immunoprecipitated from Sf9 cells expressing various recombinant HA-Plk mutants, then subjected to kinase assays using casein as substrate. Panel A shows the level of each HA-Plk mutant and the casein phosphorylation activities of the HA-Plk mutant proteins immunoprecipitated by anti-Plk antibody. The kinase reaction mixtures were electrophoresed, and the proteins were transferred onto PVDF membrane (Immobilon-P; Millipore). The two sets of gels are from two independent experiments. The top panel shows the blot subjected to immunoblotting with anti-HA antibody to determine the amount of HA-Plk present in each immunoprecipitate. The bottom panel shows the same blot exposed to detect casein phosphorylation activities. Panel B shows casein phosphorylation activities by wild-type HA-Plk (WT) and its C-terminal deletion mutant (PlkΔC). The top diagram shows the structure of the Plk region (SEQ ID No:26). The hatched box denotes the kinase domain while a closed box (amino acid residues 410–439) denotes the polo-box. PlkΔKC has been deleted for amino acid residues 356 to 604 which include the highly conserved polo-box. The bottom left panel shows immunoblotting with anti-HA antibody to determine the amount of HA-Plk and HA-PlKΔC immunoprecipitated by anti-H antibody. The bottom right panel shows detection of casein phosphorylation activities with the same blot. Cs, casein.

FIGS. 3(A–B) shows complementation of the cdc5-1 defects by ectopic expression of Plk. Panel A shows cdc5-1 mutant strain (KKY921-2B) transformed with YCplac111-GAL1-HA-PLK mutations or with YCplac111-CDC5, selected on synthetic minimal medium lacking leucine. Transformants were streaked onto either YEP-glucose (YEPD) or YEP-galactose (YEPG) plates and incubated for 3 days at the indicated temperature. Plasmids transformed are (clockwise from top): YCplac111-GAL1 vector control, YCplac111-GAL1-HA-PlkK82M, YCplac111-GAL1-HA-Plk, YCplac111-GAL1-HA-PlkT210D, and YCplac111-CDC5. Cdc5 protein was expressed under its endogenous promoter and fully complemented the cdc5-1 defect in both media, serving as a positive control. Panel B shows flow cytometric analyses of the cdc5-1 cells expressing Plk mutations. Cells were cultured at 23° C. in YEP-raffinose medium to an $OD_{600}$ of 0.8. After washing the cultures twice with water, cells were diluted in YEP-galactose medium to an $OD_{600}$ of 0.05 and cultured continuously at 37° C. for an additional 10 hrs, and were harvested, fixed, and analyzed. The first peak (arrow at left in the top left panel) in the vector panel indicates G1 cells (1N), while the second peak (second arrow from left) indicates G2/M cells (2N). Cells with more than a normal diploid (2N) DNA content (observed as a broad cell population indicated by the arrow at the right) were also apparent. Expression of the Plk WT gene or the T210D gene restored the cdc5-1 cell division defect to an extent similar to that of endogenous CDC5. CDC5 gene: YCplac111-CDC5; vector control: YCplac111-GAL1 vector; K82M gene: Ycplac111-GAL1-HA-PlkK82M; WT gene: YCplac111-GAL1-HA-Plk; T210D gene: YCplac111-GAL1-HA-PlkT210D.

Figure 4:
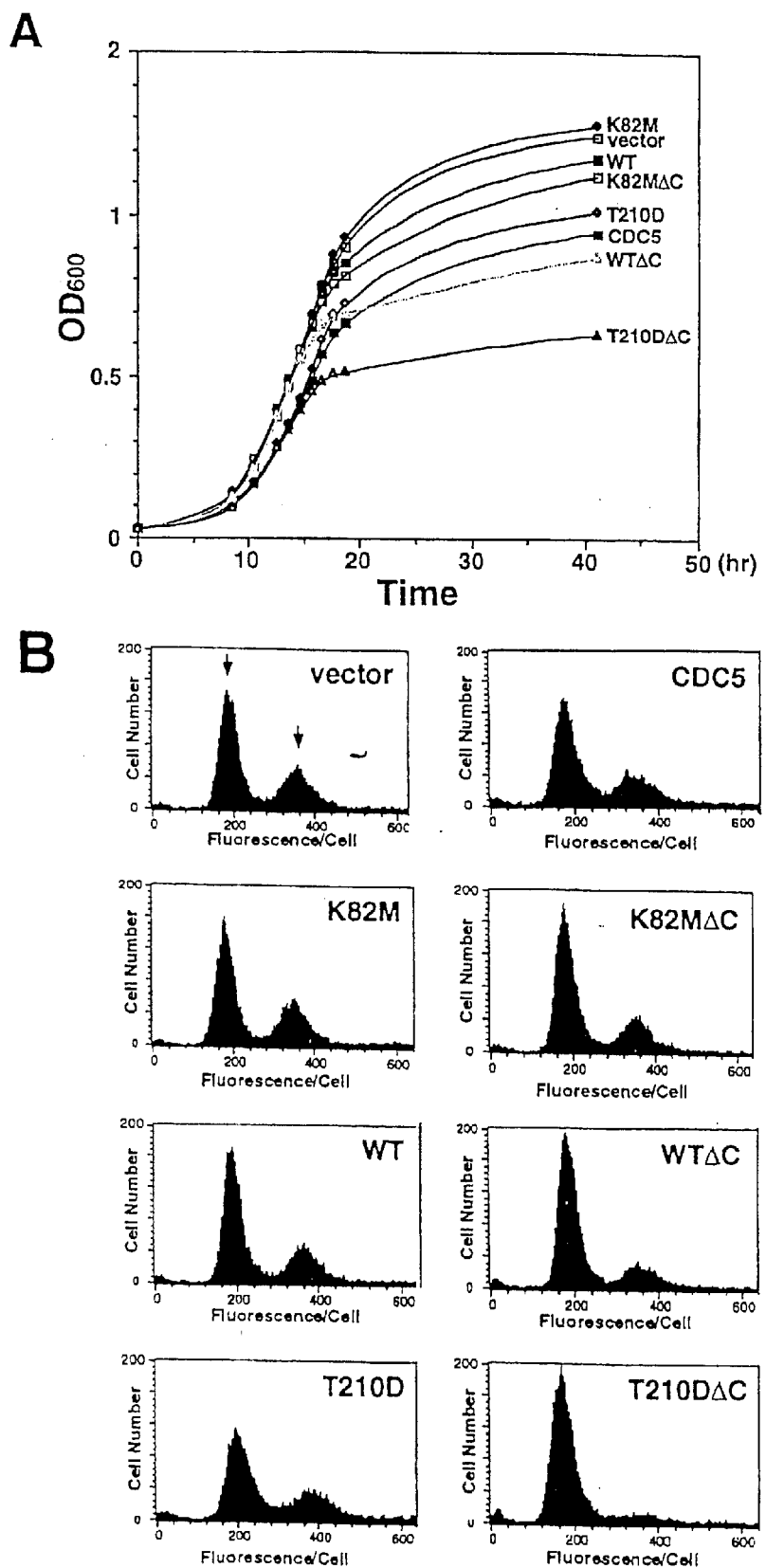
FIG. 4 panel A shows that expression of activated forms of Plk in a CDC5 wild-type background inhibited cellular proliferation. Panel B shows that expression of the activated forms of Plk resulted in the accumulation of cells in G1 phase. Vector control: YCplac111-GAL1; K82M (or K82MΔC) gene: YCplac111-GAL1-HA-PlkK82M (or -HA-PlkK82MΔC); WT gene (or PlkΔC): YCplac111-GAL1-HA-Plk (or -HA-PlkΔC); T210D gene (or T210DΔC): YCplac111-GAL1-HA-PlkT210D (or -HA-PlkT210DΔC); CDC5 gene: YCplac111-GAL1-CDC5.

FIGS. 4(A–B) panel A shows that expression of activated forms of Plk in a CDC5 wild-type background inhibited cellular proliferation. A diploid wild-type strain 1788, and derivatives that were transformed with YCplac111-GAL1-CDC5 and YCplac111-GAL1-HA-PLK mutations were cultured at 30° C. in YEP-raffinose medium to $OD_{600}$ of 0.8. After washing the cultures twice with water, cells were resuspended in YEP-galactose at an $OD_{600}$ of 0.03 and cultured continuously. $OD_{600}$ was measured at the indicated time points after shifting the cultures to YEP-galactose. Like expression of Plk active forms, overexpression of Cdc5 inhibited cellular proliferation compared to the WT and vector controls. The graphs were generated using Cricket Graph program. Panel B shows that expression of the activated forms of Plk results in the accumulation of cells in G1 phase. Cells cultured under inducing conditions for 8 hrs, when inhibition of cellular proliferation was evident, were harvested and subjected to flow cytometric analyses. The first peak (arrow on left in the top left panel) in the vector panel indicates G1 cells (2N), while the second peak (right arrow) contains G2/M cells (4N). Vector control: YCplac111-GAL1 vector; K82M gene (or K82MΔC): YCplac111-GAL1-HA-PlkK82M (or -HA-PlkK82MΔC); WT gene (or PlkΔC): YCplac111-GAL1-HA-Plk (or -HA-PlkΔC); T210D gene (or T210DΔC): YCplac111-GAL1-HA-PlkT210D (or -HA-PlkT210DΔC); CDC5 gene: YCplac111-GAL1-CDC5.

Figure 5:
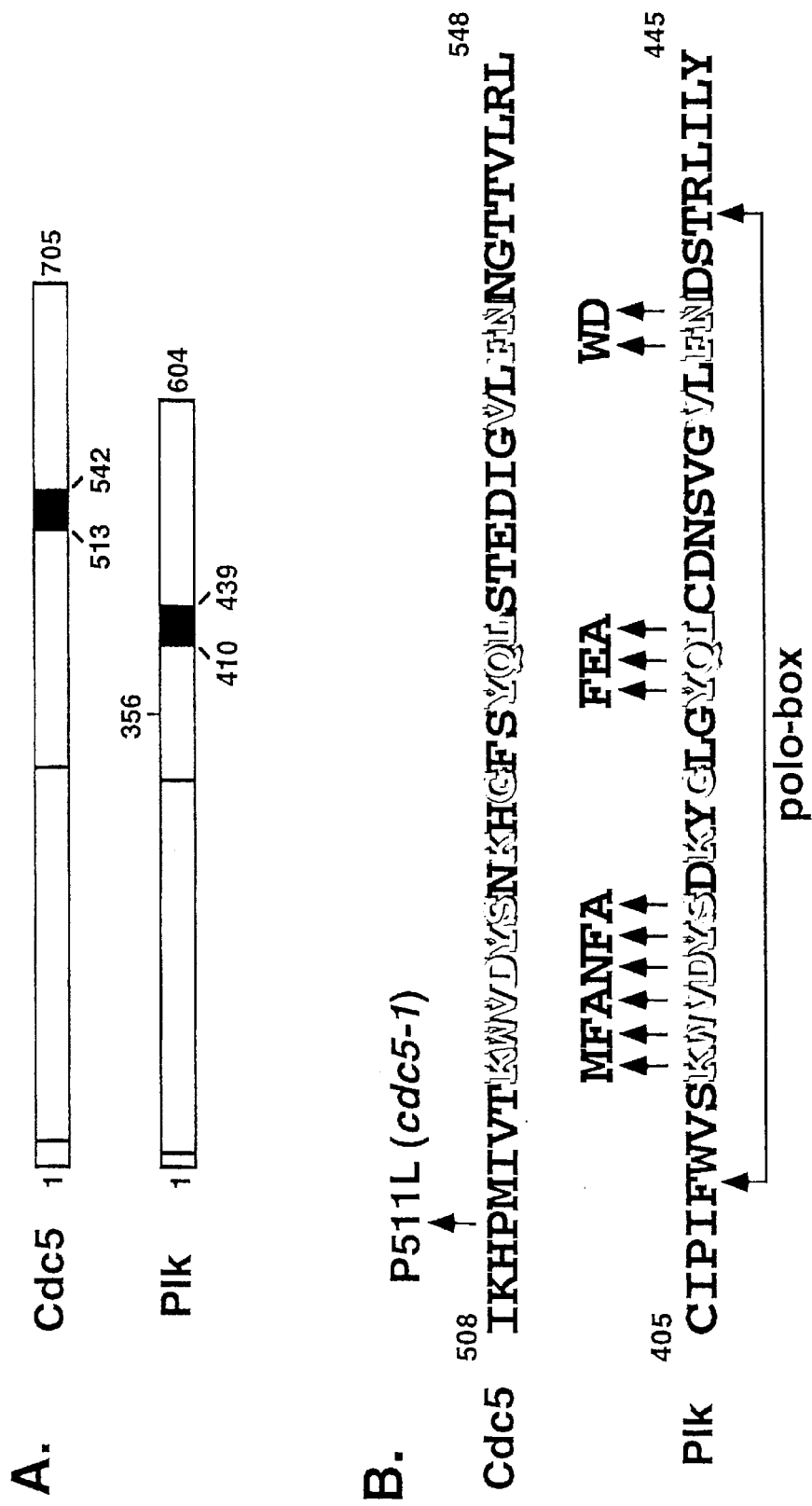
FIG. 5 panel A shows structures of the Cdc5 and Plk genes with the polo box SEQ ID Nos:18 and 19 indicated as a solid bar, and panel B shows identification of the cdc5-1 mutation site and Plk polo-box mutants.

FIGS. 5(A–B) panel A compares structures of the Cdc5 and Plk genes. The closed box denotes the polo-box and the kinase domain is in the left portion of the gene. Mutant Plk lacking the C-terminal domain (PlkΔC) is a deletion lacking amino acid residues 356 to 604. Panel B identifies the cdc5-1 mutation site and shows the polo-box mutants generated in Plk (SEQ ID NO:19). Arrows point to the residues changed by point mutation, and conserved residues are indicated in outlined letters. The Plk polo box provided here extends from residue K413 to N437 (SEQ ID NO: 2).

Figure 6:
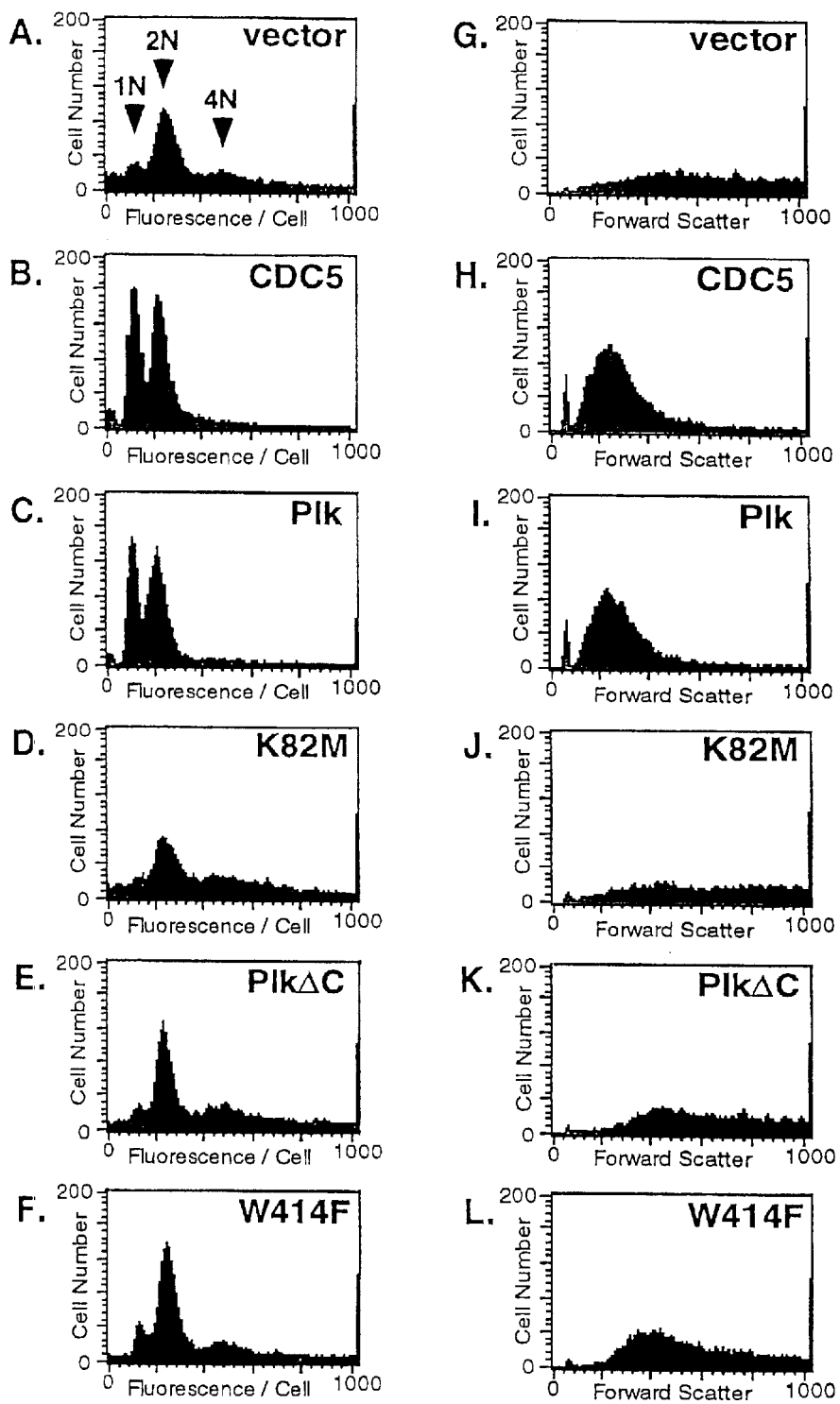
FIG. 6 shows that mutations in either the kinase ATP-binding site or the polo-box abolished the capacity of Plk to complement the cdc5-1 cell cycle defect; (A-F) show the fluorescence per cell profiles of the DNA content of the transformants in the cdcS-1 cell background, and (G-L) show the profiles of the forward scatter of each transformant.

FIGS. 6(A–H) shows that mutations in either the ATP-binding site or the polo-box abolished the capacity of Plk to complement the cdc5-1 defect. A haploid cdc5-1 mutant strain, KKY921-2B (MATa cdc5-1 leu2 trp1 ura1) was transformed with various YCplac111-GAL1-HA-PLK constructs or YCplac111-CDC5. Vector control: YCplac111-

GAL1; CDC5: YCplac111-CDC5; WT gene: YCplac111-GAL1-HA-Plk; K82M gene: YCplac111-GAL1-HA-PLkK82M; PlkΔC gene: YCplac111-GAL1-HA-PlkΔC; W414F gene: YCplac111-GAL1-HA-plkW414F. Panels A–F show the DNA content of the cdc5-1 transformants. A G1 phase cell population (haploid (1N) arrow) and a G2M phase cell population (diploid (2N) arrow) are indicated in the vector panel. Cells with a DNA content greater than 2N produced a broad peak, as indicated by the 4N arrow. Panels G to L show profiles of the forward scatter of the cdc5-1 transformants. The increase in forward scatter on the abscissa indicates increased cell size. The broad, spread out pattern observed in the cdc5-1 mutant transformed with vector (Panel G) indicates a heterogeneous population of enlarged cells, whereas wild-type cells, the cdc5-1 mutant cells complemented with the CDC5 wild-type gene (Panel H), and the cdc5-1 mutant cells complemented with the Plk gene (Panel I) gene produced a distinct bell-shaped pattern of forward scatter.

Figure 7:
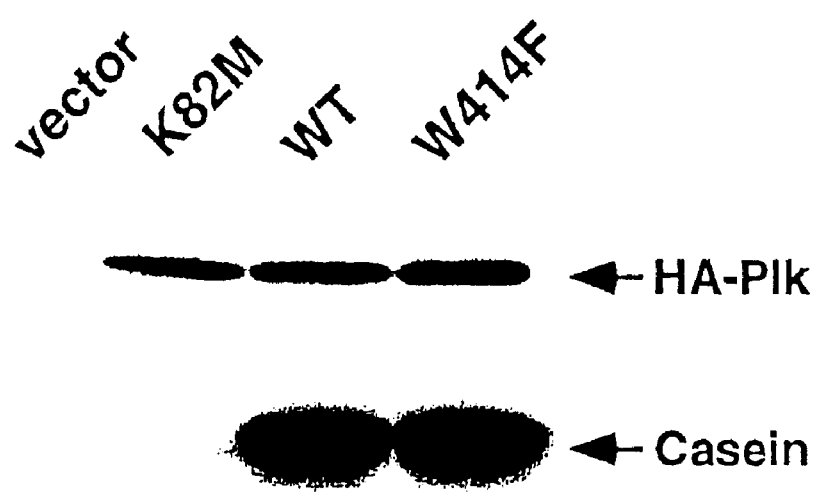
FIG. 7 shows that mutations in the polo-box retained Plk kinase activity in vitro; the upper panel shows amounts of HA-tagged Plk detected with anti-HA antibody, and the lower panel shows tagged Plk assayed for kinase activity using casein as a substrate.

FIG. 7 shows that mutations in the polo-box retained Plk kinase activity in vitro. Wild-type and mutant forms of Plk protein fusions to hemagglutinin (HA) were expressed in a cdc5-1 mutant (KKY921-2B). Upper panels show quantities of HA-tagged Plk that was immunoprecipitated from total cell extracts with affinity-purified anti-Plk antibody, electrophoresed, and detected on membranes by Western analysis with anti-HA antibody. Lower panels show HA-tagged Plk immunoprecipitated with anti-Plk antibody, and results of in vitro kinase assays performed using casein as a substrate. Vector control: YCplac111-GAL1; K82M gene: YCplac111-GAL1-HA-plkK82M; WT gene: YCplac111-GAL1-HA-Plk; W414F gene: YCplac111-GAL1-HA-PlkW414F.

Figure 8:
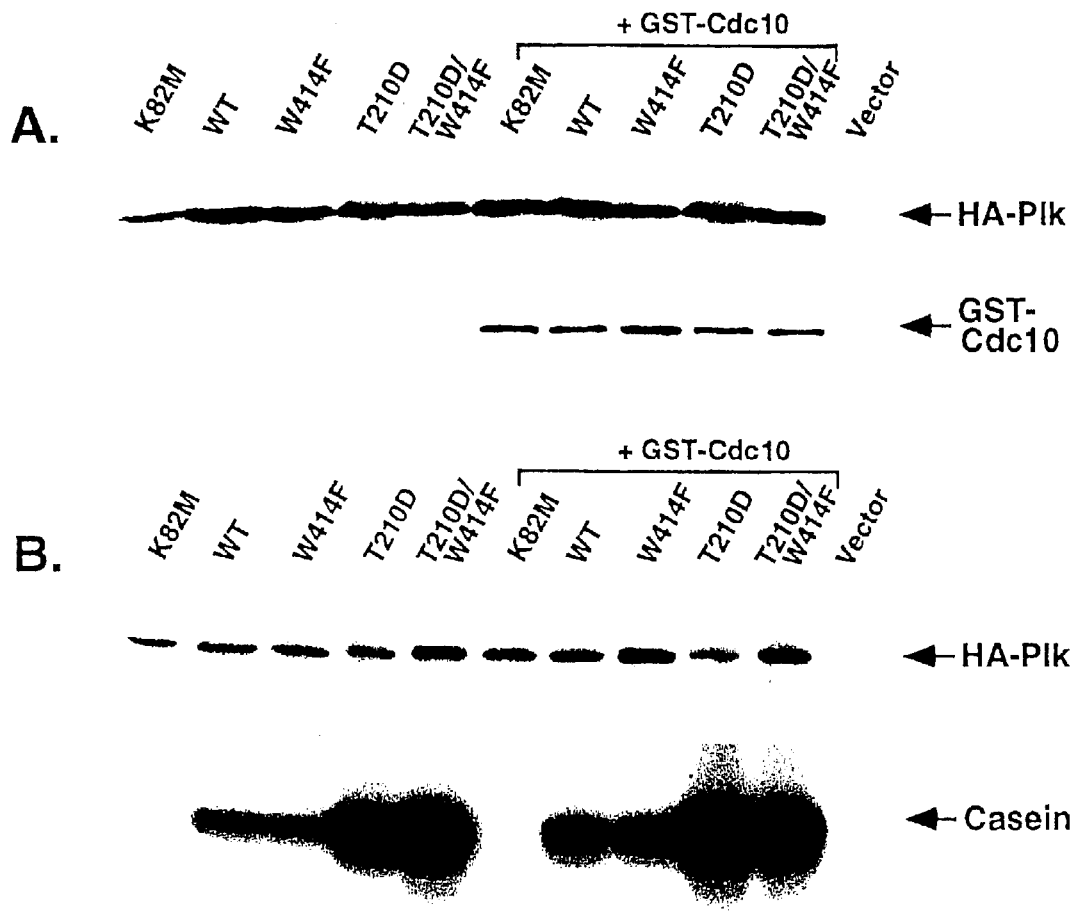
FIG. 8 shows co-expression of Plk mutants and GST-Cdc10 in the diploid wild-type *S. cerevisiae* strain 1788; panel A shows Western analysis with anti-Plk antibody of wild-type and mutant forms of Plk expressed either alone or with GST-Cdc10 (upper gel), and Western analysis with anti-GST antibody (lower gel); panel B shows Plk protein in lysates immunoprecipitated with HA-Plk (upper panel), and Plk kinase activity using casein as the in vitro substrate (lower panel).

FIGS. 8(A–B) shows co-expression of Plk mutants and GST-Cdc10 in the diploid wild-type *S. cerevisiae* strain 1788 (isogenic diploid of EG123, MATa leu2-3, 112 ura3-52 trp1-1 his4 can1'). Vector control: YCplac111-GAL1; K82M gene: YCplac111-GAL1-HA-PlkK82M; WT gene: YCplac111-GAL1-HA-Plk; W414F gene: YCplac111-GAL1-HA-PlkW414F; T210D gene: YCplac111-GAL1-HA-PlkT210D; T210D/W414F gene: YCplac111-GAL1-HA-PlkT210D/W414F; GST-Cdc10 gene: YCplac33-GAL1-GST-CDC10. Panel A shows wild-type and mutant forms of Plk expressed either alone or with GST-Cdc10. Total cellular protein was submitted to Western analysis for HA-Plk expression with anti-Plk antibody (upper panel), and for GST-Cdc10 expression using anti-GST antibody (lower panel). Panel B shows kinase assays of the cell extracts which were clarified by centrifugation at 15,000×g for 30 min, and subjected to immune complex with anti-Plk antibody. Levels of immunoprecipitated HA-Plk were detected with anti-HA antibody (upper panel). HA-Plk kinase activity was measured using casein as the in vitro substrate (lower panel).

Figure 9:
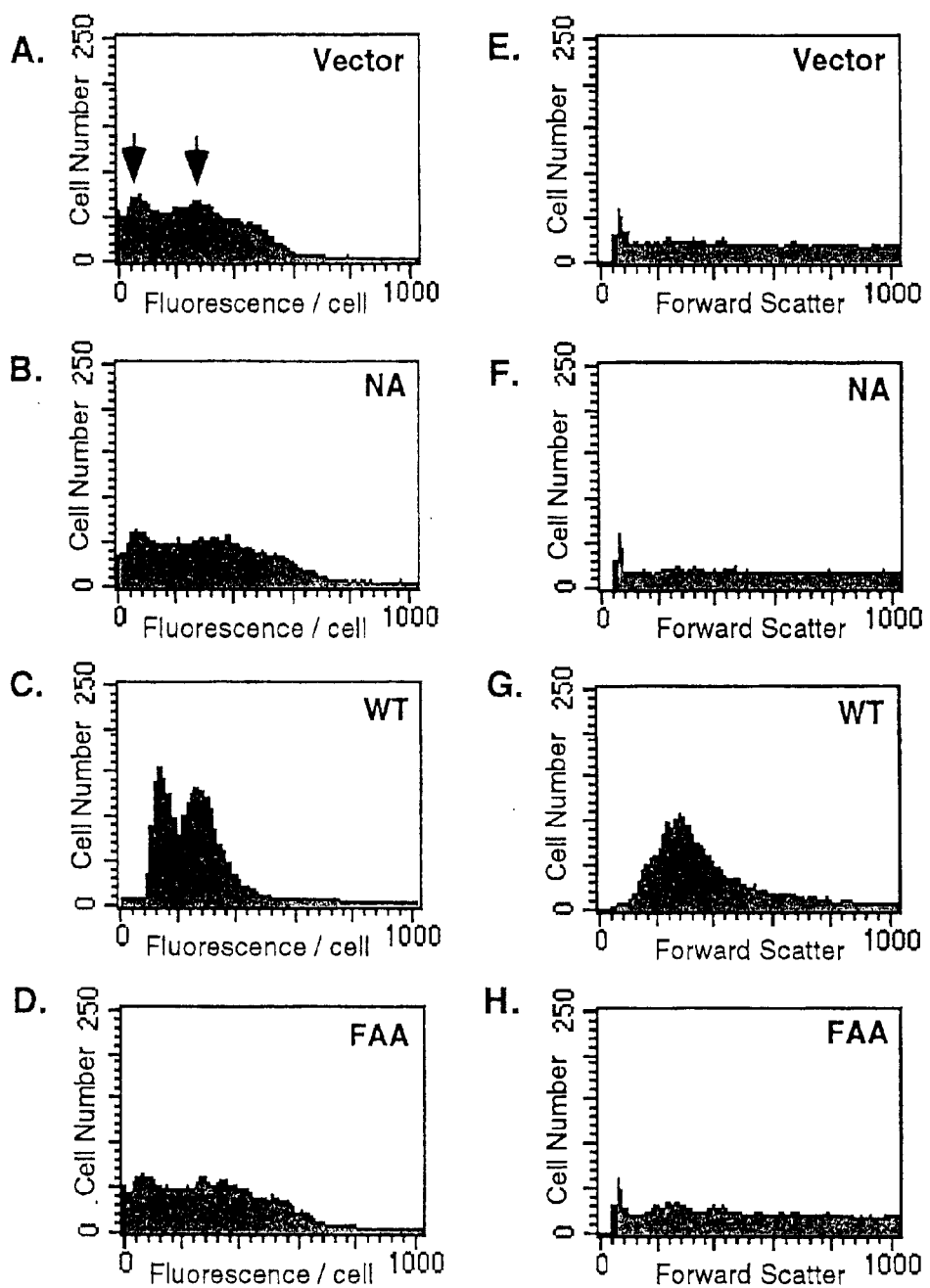
FIG. 9 shows flow cytometric analyses of the cdc5-1 cells expressing wild-type and mutant forms of Cdc5. Cells were cultured at 23° C. in YEP-glucose medium to an $OD_{600}$ of 0.5, diluted in the same medium to an $OD_{600}$ of 0.03 and cultured continuously at 35° C. for an additional 12 hrs, and samples were harvested, fixed, and subjected to flow cytometry analyses. The first peak (left arrow in panel A) represents cells with less than 1N DNA content, while the second broad peak (right arrow) represents $G_2/M$ cells with 2N DNA content. Based on their ability to grow, the cdc5-1 cells were observed to be more sensitive to an elevated temperature on YEP-glucose media than on YEP-galactose media. Under the experimental conditions, it was apparent that the majority of cells transformed with vector have lost their cell wall integrity. Vector control, YCplac111; NA gene, YCplac111-cdc5N209A; WT gene, YCplac111-Cdc5; FAA gene, YCplac111-cdc5W517F/V518A/L530A. (Panels A to D) The majority of cdc5-1 mutant cells transformed with vector arrested growth when cells achieved a 2N DNA content. The introduction of YCplac111-Cdc5 (Panel C), but not cdc5N209A (Panel B) or cdc5FAA (Panel D), complemented the cdc5-1 cell division defect, resulting in the regeneration of 1N DNA-containing populations. (Panels E to H): The increase in forward scatter along the X-axis reflects an increased cell size. The broad, spread out pattern observed in the cdc5-1 mutant transformed with the vector control (Panel E) indicates that the culture contained a heterogeneous population of enlarged cells. The cdc5-1 mutant transformed with the wild-type Cdc5 (Panel G), but not cdc5N209A (Panel F) or cdc5FAA (Panel H), produced a distinct bell-shaped pattern of forward scatter.

FIGS. 9(A–H) shows flow cytometric analyses of cdc5-1 cells expressing wild-type and mutant forms of Cdc5. Cells were cultured at 23° C. in YEP-glucose medium to an $OD_{600}$ of 0.5, and were diluted in the same medium to an OD600 of 0.03 and cultured continuously at 35° C. for an additional 12 hrs. Samples were harvested, fixed, and subjected to flow cytometry analyses. The first peak (left arrow in panel A) represents cells with less than 1N DNA content, while the second broad peak (right arrow) represents $G_2$/M cells with 2N DNA content. Based on their ability to grow, the cdc5-1 cells were more sensitive to an elevated temperature on YEP-glucose media than on YEP-galactose media. Under the experimental conditions, it was apparent that the majority of cells transformed with vector had lost cell wall integrity. Vector control, YCplac111; NA gene, YCplac111-cdc5N209A; WT gene, YCplac111-Cdc5; FAA gene, YCplac111-cdc5W517F/V518A/L530A. Panels A to D: the majority of cdc5-1 mutant cells transformed with vector were observed to have arrested growth when cells achieved a 2N DNA content. The introduction of YCplac111-Cdc5 (Panel C), but not cdc5N209A (Panel B) or cdc5FAA (Panel D), complemented the cdc5-1 cell division defect, resulting in regeneration of 1N DNA-containing cells in the population. Panels E to H: the increase in forward scatter at the X-axis indicates that cells had increased in size. The broad, spread out pattern observed in the cdc5-1 mutant transformed with the vector control (Panel E) indicates a population of cells having a heterogeneous and enlarged size. The cdc5-1 mutant transformed with the wild-type Cdc5 (Panel G), but not cdc5N209A (Panel F) or cdc5FAA (Panel H), produced a distinct bell-shaped pattern of forward scatter.

FIG. 10 shows the sequence alignment of the C-termini of M phase-specific polo kinases from four organisms, and the consensus of the original polo box designated PB1 (SEQ ID NO:1) herein, and the consensuses which are embodiments of the invention herein for each of the additional downstream polo boxes PB2 (SEQ ID NO:6) and PB3 (SEQ ID NO:7). The~at the bottom of each sequence indicates the carboxy terminal of the peptide. Analysis herein of the C-termini of Plk (SEQ ID NO:20), polo (SEQ ID NO:21), Plo1 (SEQ ID NO:22), and Cdc5 (SEQ ID NO:23) revealed these regions of amino acid sequence consensus, located downstream further towards the carboxy terminus with respect to the location of PB1. These regions include a 28 amino acid consensus identified here as PB2, and the further downstream 30 amino acid identified here as PB3 (SEQ ID NO:7). The sequence of each of the consensus regions of the polo box, or PB1 (SEQ ID NO:1), and each of PB2 (SEQ ID NO:6) and PB3 (SEQ ID NO:7), are shown FIG. 10, as are the individual amino acid sequences of these boxes in the Plk, polo, Plo1 and Cdc5 genes.

Figure 11:
FIG. 11 shows a diagram of the portions of the Plk gene generated to use as baits to isolate DNA encoding proteins that interact with the C-terminus. The designations PB2 (SEQ ID NO:6) and PB3 (SEQ ID NO:7) are based on the sequence alignment shown in FIG. 10.

FIG. 11 shows a diagram of the portions of the mammalian Plk gene generated to use as baits in the two-hybrid system (Vojtek, A. et al., 1993, *Cell* 74:2-5-214) to isolate herein DNA encoding proteins that interact with the Plk carboxy terminus. The designations PB2 and PB3 (SEQ ID NOs:6 and 7, respectively) are based on the sequence alignment shown in FIG. 10. FIG. 11 also shows regions of the Plk gene that were used as bait in two-hybrid screens to obtain Plk-interacting proteins as described in Examples 22 et seq.

FIG. 12 shows the full sequence of GRASP65 (SEQ ID No:24), with underlined residues indicating the sequence of the clones obtained from the two-hybrid system using Plk 1–400 (SEQ ID No:26) and Plk 323–499 (SEQ ID No:26) as bait. GRASP65 can interact with protein GM130 at the double underlined residues; and SLL indicated putative Plk phosphorylation sites in GRASP65.

FIG. 13 shows the sequence of CCT-ε (SEQ ID No:25) in cDNA cloned by the two-hybrid method using Plk residues 323–499 (SEQ ID No:26) as bait. The data show that DNA encoding residues 11–139 (underlined in FIG. 13) was observed from the clone.

Definitions

As used in this description and in the accompanying claims, the following terms shall have the meanings indicated unless the context otherwise requires.

The terms "protein", "polypeptide", and "peptide" shall have the same meaning. A specific protein compositions can be described as having a particular amino acid sequence, which can be written as a string of amino acids using the three letter or one letter code, each defined herein. The letter X in an amino acid sequence denotes for each position so designated that an unspecified amino acid residue can be allowed for that position. A polypeptide can be synthesized using solid state chemical synthesis procedures, or can be obtained from nature from a wild type (WT) or from a genetically engineered cell.

"Subject" shall mean a mammal including a human. In a preferred embodiment for a method to obtain a product for end use in a subject, for example for treatment of a cancer, it is preferable to use a particular sequence of the invention, for example, a polo box sequence from a mammal, for example, SEQ ID NO: 2 encoding the Plk sequence. In another embodiment, for example, for use to treat a fungal infection of a mammal, it is preferred that the polo box sequence be obtained from a fungus, for example, the *S. cerevisiae* CDC5 sequence (SEQ ID NO:3).

The term "polynucleotide" means a polymer of nucleotides having a sugar-phosphodiester backbone with a sequence of particular bases each covalently attached to the sugar, wherein the sugar is deoxyribose or ribose. A polynucleotide can be synthesized using solid state chemical synthesis procedures, for example using a device available from PerSeptive Biosystems (Framingham, Mass.) division of Perkin-Elmer, or can be obtained by isolation from nature from a wild type (WT) or from a genetically engineered cell using standard molecular biology techniques, e.g., as described by Sambrook et al, *Molecular Cloning: A Laboratory Manual*, 2nd Ed., 1989, Cold Spring Harbor Laboratory Press, Cold Spring Harbor, N.Y.

The term "nucleic acid" refers to a polynucleotide that can be obtained from a wild type or genetically engineered cell, or can be identical in sequence to that which can be obtained from a cell, or can be synthesized chemically. A particular nucleotide residue in a sequence is covalently attached to the neighboring nucleotides by phosphodiester internucleotide bonds, however one or more bond can be substituted with an analog that is resistant to digestion with a nuclease, for example, an internucleotide bond can be a peptide bond or a phosphorothioate bond (Egholm, M. et al., *J. Am Chem. Soc.*, 114:1895–1897, 1992).

The term "ectopic" refers to expression of a gene isolated from one cell, for example the Plk gene for mammalian polo kinase, in a different cell background, for example, in a yeast cell, the expression of the gene being regulated differently than that of an endogenous similar gene native to the cell.

A polynucleotide of the invention for design of an antisense therapeutic agent is preferably single-stranded, as is a polynucleotide for triple strand therapy. Methods of design of such therapeutic agents to be resistant to nuclease digestion are well known to those of skill in the art, and this art for use for modulation of expression of a gene in a cell is described (Goodchild, J., *Bioconj. Chem.* 1:165–187, 1990; Iversen, P., in *Antisense Research and Applications*, Crooke, S. Ed., CRC Press, Ann Arbor, Mich., 1993, pp 462–469).

The term "fusion protein" refers to a composition which is a polypeptide gene product of a natural or a genetically engineered gene, yielding a polypeptide comprising a first amino acid sequence covalently linked and in the same translation frame with at least a second amino acid sequence, the several amino acid sequences not generally being found together on the genome of any wild-type organism. The hybrid genes used in a two-hybrid selection system encode fusion proteins. Methods of genetic engineering known to one of skill in the art can be found described in the literature, see for example Ausubel, F. et al., *Short Protocols in Molecular Biology*, 3rd Ed., 1995, Cold Spring Harbor Laboratory Press, Cold Spring Harbor, N.Y., and Sambrook et al., supra.

The term "filamentous bacteriophage" means an infectious bacterial virus that is an intracellular parasite of a bacterial cell, the virion having a filament-like morphology. A preferred embodiment of a filamentous bacteriophage is a filamentous coliphage which grows using cells of an *Escherichia coli* K-12 $F^+$ strain as a host. Engineered derivatives of the most preferred filamentous bacteriophage are described in U.S. Pat. No. 5,403,484 by R. Ladner et al. phage stains which are genetically engineered to cause expression and display of an inserted gene product as a fusion to a coat protein of the phage. The polo kinases or particular portions comprising features thereof of the present invention can be used as an affinity material immobilized onto a solid surface, and a library of peptides displayed as fusions to a coat protein of a phage can be screened to obtain peptides that have high affinity for the polo kinase feature.

The term "vector" means a nucleic acid molecule capable of replicating in a cell and of being genetically engineered. The term encompasses circular plasmid DNA for expression of engineered genes carried on it in a yeast cell or in an Sf9 insect cell, and it encompasses nucleic acid capable of being packaged into a virus coat, for example, a retroviral coat, for delivery of a nucleic acid to a site in a subject for gene therapy or for antisense therapy. Retroviral vectors, insect cell expression vectors, and yeast expression vectors are described in Ausubel et al., supra, as well as standard methodologies for use of these vectors.

The terms "restrictive" and "permissive" conditions refer to culture conditions for conditional lethal mutant cells, for example, the cdc series of yeast cell division cycle mutants such as those described herein and in the claims, which can grow at 23 but not at 35 or 37 degrees C. "Non-permissive" and "restrictive" shall mean the same thing.

The term "complementation" has its standard genetic meaning, such that positive complementation restores a wild type (WT) phenotype, in this case, ability to grow at the restrictive condition. A complementing gene may be under control of a non-native or heterologous regulatory element, such as the yeast GAL1 promoter or a tet repressor, in which case expression of the gene is induced by the addition of galactose or a galactose analog to the medium, or is repressed by the presence of tetracycline or a tetracycline analog, respectively. Complementation of a conditional lethal temperature-sensitive gene by a gene expressed under regulation of GAL1 permits cell growth in the presence of the inducing sugar at the non-permissive (restrictive) condition.

The term "protein kinase" refers to an enzyme capable of adding a phosphate group to one or more threonine and serine residues, or to tyrosine residues, of a particular substrate protein or proteins, in which case only specific thr and ser or tyr residues are so phosphorylated. Similarly, the term "protein phosphatase" refers to an enzyme capable of removing phosphates from residues in the specific substrate protein of that phosphatase. The respective enzymatic activities of kinases and phosphatases can be assayed using a non-specific protein substrate, such as casein (cs) for serine/threonine kinases.

The term "cytokine" refers to a protein effector that causes stimulation of cell growth or differentiation or both, and has specific classes of target cells which have receptors for the specific cytokine, and can respond not only by growth and differentiation, but also by expression and production of additional classes of proteins. Cytokines include without limitation lymphokines, interleukins, growth factors and interferons.

The term "polo kinase binding partner" peptide (PKBP) shall mean a portion of a protein capable of binding to a feature of a polo kinase in vivo, as such binding occurs normally in a wild-type cell. A PKBP can be a feature of a protein including a substrate for polo kinase function. Alternatively, a PKBP can bind specifically to another cell component such as a protein, so that the complex acquires a function that is different from the functions identified for each of the individual components.

The term "polo box binding inhibitor" shall mean a peptide, a peptide analog, a peptidomimetic or a low molecular weight molecule which binds specifically to the features of any of the polo boxes PB1, PB2, or PB3 (SEQ ID NOs: 1, 6, or 7, respectively) as these interact with a feature of another protein or cell component, to disrupt the interaction. A drug obtained from an embodiment of the invention which is a method of screening for a therapeutic agent can be a polo box binding inhibitor.

The term "peptide analog" shall mean a compositions comprising amino acid residues, and includes one or more components which are amino acid derivatives and/or amino acid analogs comprising part or the entirety of the residues for any one or more of the 20 naturally occuring amino acids indicated by that sequence. For example, in an amino acid sequence having one or more tyrosine residues, a portion of one or more of those residues can be substituted with homotyrosine. Further, an amino acid sequence having one or more non-peptide or peptidomimetic bonds between two adjacent residues, is included within this definition.

The term "peptidomimetic" shall mean a synthetic analog of an oligopeptide having similar properties of size, shape, and hydrophobic and hydrophilic components, however having non-peptide alternative bonds which are resistant to protease degradation.

Methods and uses

Yeast genetic techniques

Technologies for genetic and molecular manipulations of yeast are familiar to those of skill in the art, and are summarized in numerous manuals, for example, Ausubel, F. et al., Eds. "Short Protocols in Molecular Biology", 3rd Ed., 1995, New York:Wiley. Preparation of the specific strains, vectors, media and techniques used in embodiments of the invention are described in Lee, K. et al, 1997 *Mol. Cell. Biol.* 17:3408–3417, and Lee, K. et al., 1998, *Proc.Natl.Acad.Sci. USA* 95:9301 –9306, the contents of both of which are hereby incorporated by reference, and in the Examples herein.

The demonstration herein that the mammalian gene Plk (SEQ ID No:26) encoding a polo kinase can function in yeast and can complement mutation cdc5-1 of a homologous polo kinase gene of yeast, indicates that genes for polo kinases of interest found in unwanted cells of a subject can be isolated and similarly studied in these yeast strains. It is an object of an embodiment of the present invention to clone and isolate polo kinase genes from fungal and protozoan pathogens, and from helminths, arthropods, and tumor cells of subjects, and to identify the polo box sequences of the polo kinase genes found in these unwanted cells. The methods of the invention can be used to thereby obtain an inhibitor of a function of the polo kinase of the unwanted cell, using the *S. cerevisiae* strains as recipient cells for screens.

High-throughput screens for drugs that inhibit polo kinases

An object of the present invention is the use of high-throughput screens (HTS; Dutton, G., 1999, *Gen.Eng.News* 19(5):1) with the cell lines, mutants, plasmid constructs, and methods of the present invention, to identify potential drug candidates from among an excess of non-candidates in large libraries of synthetic organic candidate chemicals. An optimized robot for chemical analysis (ORCA; Beckman-Coulter, Fullerton, Calif.) can be used for synthesis and analysis of chemical libraries (T. Rooney, 1999, *Today's Chem. Work* 8:17–24). Methods of HTS, including synthesis of chemical libraries and culture and assay of screen organisms in sterile multi-well plastic dishes containing for example 96 or 354 wells per dish, robots for delivery of samples to each well using devices such as automated multi-pipeters, and for processive manipulation of each dish, and for computerized reading of growth as optical density or production of light absorbant material at a given wavelength in each well, are well known to those of ordinary skill in the art of HTS. The screens that are embodiments of the invention herein are suitable for automated and robotic high throughput drug screening methods. Programs for collection, analysis, storage and retrieval of growth data for each chemical at each condition of temperature and cell strain are available.

Such methods can be used to monitor potential inhibition of growth of yeast strains at a non-permissive temperature in the presence and absence of drug candidates, and to record the control growth of these strains at the permissive temperature in the presence and absence of the candidate chemical, and of control strains under these conditions. These screens can also be adapted to further screening of chemical derivatives of a successful drug candidate that would be designed to have improved pharmaceutical properties, for example, longer half-life in vivo due to modification or derivatization of the chemical structure to resist protease degradation, greater activity against the unwanted cell, and lower toxicity in a test animal in a pre-clinical trial.

These methods of screening enable the practice of the embodiment of the invention herein to obtain a drug candidate which is not lethal due to generalized broad inhibitory activity, but is a polo box inhibitor, or a polo kinase binding partner, which interferes with a specific essential in vivo function of the polo kinase protein.

Pharmaceutical Methods

Following identification of a potential drug candidate, the in vitro testing of a polo box inhibitor can be achieved using target cells as indicated herein. For example, an anti-fungal or anti-protozoan agent can be tested in culture with the pathogenic fungus strain or protozoan species for which the potential agent has been isolated to treat. Animal model systems can be employed, for example, to test anti-fungal, anti-protozoan, anti-helminth and anti-arthropod agents. For many of these animal model tests, one anatomical feature can be used to test the agent, and another can be left untreated, or uninfected. Animal models of tumor growth, for example, transgenic animals having human oncogenes, can be employed. Further, standard cell lines of transformed cells carrying oncogenes such as ras or p53 can be used to test anti-tumor agents, with untreated cells and normal cells constituting relevant controls.

A drug candidate composition of the present invention can be administered by a variety of methods known in the art as will be appreciated by the skilled artisan. The active compound can be prepared with carriers that will protect it against rapid release, such as a controlled release formulation, including implants, transdermal patches, microencapsulated delivery systems. Many methods for the preparation of such formulations are patented and are generally known to those skilled in the art. See, e.g., *Sustained and Controlled Release Drug Delivery Systems*, J. R. Robinson, Ed., Marcel Dekker, Inc., NY, 1978. Drugs can be administered to be released at a localized site of a tumor, for example, a brain tumor, by use of an drug delivery implant device having a reservoir of the drug to be released over an extended period.

Therapeutic compositions for delivery in a pharmaceutically acceptable carrier are sterile, and are preferably stable under the conditions of manufacture and storage. The composition can be formulated as a solution, microemulsion, liposome, or other ordered structure suitable to high drug concentration.

A polo kinase binding partner peptide can be delivered as a genetic element, for example, DNA encoding expression and translation of the peptide. DNA can be delivered as a "naked" vector, or can be encapsulated into a viral vector, for example, an adenoviral vector. Techniques for introduction of DNA into mammalian cells are known to those of ordinary skill in the art, and are reviewed by Ausubel, F. et al, , Eds. "Short Protocols in Molecular Biology", 3rd Ed., 1995, New York:Wiley. A polo box inhibitor can be an antisense polynucleotide, for example, which can inhibit translation of an mRNA encoding a polo kinase or a portion thereof, for example, mRNA encoding a polo box or portion thereof, or mRNA encoding a polo kinase binding partner peptide. Antisense polynucleotides are preferably composed of nucleotide analogs that are resistant to nucleases, for example, having one or more internucleotide bonds being a peptide or a phosphorothioate bond rather than a phosphodiester bond.

Dosage regimens can be adjusted to provide the optimum desired response (e.g., a therapeutic response). For example, a single oral dosage or a single bolus can be administered, several divided doses can be administered over time, or the dose can be proportionally reduced or increased as indicated by the exigencies of the disease situation.

In general, a preferred embodiment of the invention is to administer a suitable daily dose of a therapeutic polo box inhibitor composition that will be the lowest effective dose to produce a therapeutic effect, for example, mitigation of symptoms. The therapeutic inhibitor compounds of the invention are preferably administered at a dose per subject per day of the minimum amount of the inhibitor per kilogram of the subject per day which can produce a remediation of symptoms, for example, remission of symptoms of fungal infection such as presence in the oral or genital tract of substantial numbers of cells of *Candida albicans;* remission of symptoms of protozoan infection such as malarial fever episodes or *Entamoeba histolytica* diarrhea; or regression in size of a tumor. A reduction in infestation by an arthropod can be determined by visual inspection and by reduction in symptoms such as itch and pain.

A physician or veterinarian having ordinary skill in the art can readily determine and prescribe the effective dose of the pharmaceutical composition required. For example, the physician or veterinarian could start doses of the compound of the invention employed in the pharmaceutical composition at a level lower than that required in order to achieve the desired therapeutic effect, and increase the dosage with time until the desired effect is achieved.

In another preferred embodiment, the pharmaceutical composition includes also an additional therapeutic agent. Thus in a method of the invention the pharmaceutical composition can be administered as part of a combination therapy, i.e. in combination with an additional agent or agents. Examples of materials that can be used as combination therapeutics with the inhibitors for treatment of a fungal infection as additional therapeutic agents include: an identified antifungal agent such as nystatin, mycostatin, or griseofulvin. An anti-tumor drug candidate of the present invention can be used in combination with an anti-cancer agent such as methotrexate or adriamycin; or a cytokine. An anti-protozoan agent can be used in conjunction, for example with an anti-malarial agent such as chloroquine.

An additional therapeutic agent can be a cytokine, which as used herein includes without limitation agents which are naturally occurring proteins or variants and which function as growth factors, lymphokines, interferons, tumor necrosis factors, angiogenic or antiangiogenic factors, erythropoietins, thrombopoietins, interleukins, maturation factors, chemotactic proteins, or the like. Preferred combination therapeutic agents to be used with the composition of the invention and which are cytokines include interleukin-4 and interleukin-10. A therapeutic agent to be used with the composition of the invention can be an engineered binding protein, known to one of skill in the art of remodeling a protein that is covalently attached to a virion coat protein by virtue of genetic fusion (Ladner, R. et al., U.S. Pat. No. 5,233,409; Ladner, R. et al., U.S. Pat. No. 5,403,484), and can be made according to methods known in the art. A protein that binds any of a variety of other targets can be engineered and used in the present invention as a therapeutic agent in combination with a polo box inhibitor or polo box binding partner peptide or peptide analog of the invention.

A therapeutically effective dosage preferably reduces symptomology by at least about 20%, more preferably by at least about 40%, even more preferably by at least about 60%, and even still more preferably by at least about 80%, relative to untreated subjects.

The therapeutic compounds of the invention can be used to treat symptoms of a fungal disease such as athlete's foot, yeast infection, and various skin infections, including infection by Candida, Lichen, Trichophyton, Epidermophyton, and Microsporum. An anti-cancer agent can be used to treat tumors of the brain, lung, skin, breast, ovary, prostate, and other solid neoplasms. An anti-arthropod agent can be used to treat head and body lice, ear mites, and other infestations.

Two-hybrid systems

Yeast two-hybrid systems are methods of identifying those proteins (commonly referred to as "fish" or "prey") in a cell that interact with a particular protein of interest (called "bait"). these techniques and particular examples are known to one of ordinary skill in the art of yeast molecular genetics, and are described by Vojtek, A et al., 1993 *Cell* 74: 205–214, and reviewed in Brent, R. et al., 1997 *Ann. Rev. Genet.* 31: 663–704.

The yeast two-hybrid system relies on the interaction of two fusion proteins to bring about the transcriptional activation of a reporter gene or a selectible marker. One fusion protein comprises a preselected bait protein fused to the DNA binding domain of a known transcription factor. The second fusion protein comprises a population of polypeptide prey expressed from a cDNA library fused to a transcriptional activation domain. In order for the reporter gene to be activated, the polypeptide from the cDNA library must bind directly to the preselected target protein. Yeast cells expressing the reporter gene or the selectible marker can be differentiated from other cells by the conditions of growth so that they can form colonies or grow in liquid culture under certain conditions, while the majority of cells cannot grow. The cDNA encoding for the interacting polypeptides can be easily isolated and sequenced.

Several transcriptional activation modules have been identified as described by Mendelsohn, A. et al., 1994, *Curr. Opinions in Biotech.* 5:482–486, and by Crabtree et al (WO 95/02684). Any of these are suitable for use in a two-hybrid system. A wide variety of transcriptional activation domains can be used including the yeast transcriptional activator and DNA binding proteins and GAL 4, GCN4 and, in combination with the viral promoter VP16. The DNA encoding transcriptional activator modules are incorporated into vectors that are capable of being expressed in eukaryotic cells. Adjacent to and downstream of these sequences is inserted DNA encoding a target bait protein on a first expression vector, and DNA encoding a library including unknown gene prey products on a second expression vector, such that both proteins are expressed by specifically inducing the regulation of these genes in the eukaryotic cell. They do not dimerize however, unless a prey protein was successfully cloned, the prey protein able to bind with specificity and affinity to the particular bait protein.

Example 1 describes protein kinase activity of mammalian Plk wild-type and mutant protein expressed in insect Sf9 cells on a baculovirus vector. The mutants expressed in Sf9 cells included a mutant of amino acid residue Thr210, a key amino acid located in the polo box SEQ ID No:2 of the C-terminus end of the Plk polo kinase.

Examples 2 through 13 describe properties of yeast cells containing the mammalian Plk gene encoding murine polo kinase, expressed in wild-type Cdc5 cells or cdc5-1 mutant cells of *Saccharomyces cerevisiae*.

Example 2 examines the ability of the mammalian Plk gene (SEQ ID No:26) to complement a variety of phenotypes associated with the yeast cdc5-1 mutation. Since the CDC5 gene is the only polo kinase found in yeast cells, yeast is a choice model system to study the function of a mammalian polo kinase. Data in Example 2 show that the mammalian Plk gene or a mutant of this gene having aspartic acid instead of threonine at residue 210 were capable of complementing phenotypes associated with cdc5-1.

Example 3 shows that the amount of Plk kinase activity correlated with the ability of the Plk gene to complement mutation cdc5-1. Two mutations of Plk (SEQ ID No:26) at the Thr210 residue, one to Asp and another to Val, reveal that 210 is a key regulatory residue. Thus, each of these mutations has a different effect on the specific kinase acitivity of Plk. This residue can be subject to activation by phosphorylation, for example, by an upstream kinase involved in initiating events of mitosis, and deactivation by a phosphatase activity.

The mammalian Plk gene (SEQ ID No:26) was expressed in yeast cells such that its expression was inducible by addition of galactose or a galactose analog to the growth medium. Example 4 shows that ectopic expression of Plk caused the cells to accumulate in the G1 stage. This accumulation of 1N yeast cells was not seen however in cells having a cdc5-1 background. Inhibition of cellular proliferation due to accumulation of cells blocked at G1 correlated with the expression of activated Plk.

Example 5 shows that the location of Plk kinase activity in large sedimentible cell structures. In Example 6, Plk expression was shown to induce multiple septation structures. Example 7 shows that a functional polo box (SEQ ID No:2) was required for successful complementation of the cdc5-1 mutation. This mutation was further shown in Example 8 to alter the proline residue at position 511 to substitute leucine at the upstream boundary of the polo box in the yeast polo gene.

In Example 9, the wild-type yeast CDC5 and mammalian Plk genes were shown to complement the defect in cell size and shape of yeast cdc5-1 cells. However, neither Plk mutant W414F nor PlkΔC conferred the wild-type cell morphology, demonstrating the requirement that both the kinase and the polo box functional sequences be present in the cell to obtain a phenotype of normal morphology.

Example 10 shows that ectopic constitutive expression of polo kinase by the Plk T210D mutant caused an unusual elongated bud cell phenotype. Expression of the PlkΔC mutation however did not cause this phenotype in spite of the kinase activity, indicating that a polo box is necessary for expression of this phenotype.

Septin protein, the product of Cdc10, affected the frequency of cells having this unusual bud phenotype. Furthermore, this was confirmed by showing in Example 11 that the presence of the Plk W414F mutation curtailed the elongated bud phenotype, so that a functional polo box (SEQ ID No:2) was required to obtain the elongated bud phenotype.

The location of Plk protein yeast cells was further investigated using gene fusions to the gene encoding green fluorescent protein. In this manner it was shown that the green fluorescent protein was localized to distinct dots in the cytoplasm at one or two locations in the bud neck, consistent with a localization in mitotic structures, for example the mitotic spindle. The results with various genetic backgrounds indicates that Plk was localized to both single poles and bud-neck filaments. Staining of septin protein Cdc10 with rhodamine-conjugated goat anti-rabbit IgG to visualize rabbit polyclonal anti-Cdc10 antibodies showed that Cdc10 and Plk colocalized to the same mitotic structures. This colocalization was shown in Example 13 to require both domains of Plk.

Examples 14–19 examined the yeast polo kinase gene Cdc5 with respect to its kinase activity and polo box (SEQ ID NO:13) domain structure and function. Example 14 shows that the presence of both of these domains in functional form was required for complementation of the cdc5-1 mutation. Example 15 shows that mutations in the polo box, particularly the "FAA" triple mutant having three mutations W517F, V518A, and L530A, using here the convention of the wild-type indicated by the one letter code to the left of the residue number followed by the inserted substitution residue to the right, did not complement the cdc5-1 defect. Further, these mutations cause failure of the polo kinase protein to locate to the spindle poles and cytokinetic neck filaments.

Additional septal structures were shown in Example 16 to have been induced by ectopic expression of the yeast Cdc5 protein. In Example 17 the Cdc5 protein was shown to localize to the additional cytokinetic septal structures. Both domains of the Cdc5 protein were required in Example 18 to induce abnormally elongated buds. Further, the triple FAA mutation of the yeast polo box (SEQ ID No:3) did not affect expression level or kinase activity, as shown in Example 19.

FIG. 11 shows regions of the Plk gene that are used as bait in two-hybrid screens to obtain Plk-interacting proteins as described in Examples 22 et seq. Example 23 describes identification of the Golgi reassembly stacking protein Grasp 65 (SEQ ID NO: 24), amino acid residues 6–114 of which were found to interact in a polo dependent fashion with each of Plk 1–400 and Plk 323–499.

Additional examples of cell proteins that interact with polo kinase, as identified by isolation of clones from a library of fish using various portions of Plk as bait in the two-hybrid system are shown in Examples 23 through 26. These include the chaperonin-containing-TCP (CCT-ε), a carboxy terminal sequence of Plk, and a translationally controlled tumor protein TCTP/p23 (SEQ ID No:27). Thus a set of polo kinase binding partner peptides, or PKBPPs, have been identified as novel targets for drugs discovery screens. Further, a working system for identification of further such targets has been demonstrated, which can also be used with each of the known targets of Plk interaction to identify small chemical drugs as therapeutic agents to inhibit the interaction.

EXAMPLES

Materials and Methods

The following materials and methods were used through the Examples.

Strains, growth conditions, and transformations.

Yeast mutant cdc5-1 strains are available from the American Type Culture Collection (Rockville, Md.), for example ATCC #46,590 D473H cdc5-1/cdc5-1.

Other yeast strains used in this study are 1788 (isogenic diploid of EG123, MATα leu2-3,112 ura3-52 trp1-1 his4 can1$^r$; Siliciano, P. G., et al, *Cell* 37:969–978) and KKY921-2B (MATa cdc5-1 leu2 trp1 ura1; Kitada, K., 1993, Mol. Cell. Biol. 13:4445–4457). Yeast cells were cultured in YEP (1% yeast extract, 2% Bacto-peptone) supplemented with 2% glucose, 2% raffinose (Sigma, St. Louis, Mo.), or 2% galactose (J. T. Baker, Phillipsburg, N.J.) as required. Synthetic minimal medium (Sherman, F., et al., 1986. *Methods in yeast genetics.* Cold Spring Harbor Laboratory, Cold Spring Harbor, N.Y.) supplemented with the appropriate nutrients was employed to select for plasmid maintenance. Yeast transformation was carried out by the lithium acetate method (Ito, H., et al., 1983, *J. Bacteriol.* 153:163–168).

Generation of Plk mutants and expression in Sf9 cells.

Site-directed mutagenesis in a murine PLK cDNA was carried out using the Sculptor in vitro mutagenesis system (Amersham International plc, Buckinghamshire, England). Mutations at the indicated sites were generated using a pBluescript II KS(+)-PLK construct. An 1.4 kb-SacI fragment isolated from each partially digested mutant clone was ligated into pAC702-HA-PLK (Lee, K. S., et al., 1995, *Mol Cell Biol* 15:7143–7151) digested with SacI and dephosphorylated. The pAC702-HA-PLK mutant clones were sequenced to confirm the presence of the mutations in the PLK coding sequence. A C-terminally deleted Plk WT (PlkΔC, deleted of residues 356–604) was constructed by digesting the pAC702-HA-PLK with SmaI (using an additional SmaI site in the polylinker at the 3' of PLK cDNA) and self-ligating the resulting fragment, to delete amino acid residues 356 to 604 from the PLK coding sequence. Various Plk constructs were transfected into Sf9 cells using BaculoGold (Pharmingen, San Diego, Calif.).

Expression of Plk mutants in yeast cells.

Ycplac111-GAL1 vector was generated by inserting an 800-bp EcoRI-BamHI fragment of GAL1 promoter sequence from YEplac181-GAL1 vector, a 0.8-kb GAL1 promoter sequence inserted at the EcoRI and BamHI sites of YEplac181 vector (Gietz, R. D., *Gene* 74:527–534) into the corresponding sites in the multiple cloning sites of YCplac111 vector. A 2.4-kb DraI fragment which contains the entire coding sequence and 3' untranslated region of HA-PLK was isolated from each pAC702-HA-PLK mutant construct and cloned into YCplac111-GAL1 digested with XbaI end-filled, and dephosphorylated. To construct C-terminally deleted Plk mutants, YCplac111-GAL1-HA-PLK clones were digested with SmaI (an additional SmaI site at the 3' of PLK cDNA) and self-ligated, resulting in the loss of amino acid residues 356 to 604 from the PLK coding sequence.

To express various Plk mutant proteins in *S. cerevisiae*, yeast transformant cells harboring each construct were grown at 30° C. in YEP-raffinose to an OD$_{600}$ of 0.8. All the cdc5-1 transformants were cultured at 23° C. Cells were washed twice with water and resuspended in YEP-galactose at an OD$_{600}$ of 0.05 and cultured continuously. To examine complementation of the cdc5-1 defect by Plk expression, cells were cultured at 37° C.

A 2.82-kb fragment of CDC5, which contains the entire coding sequence, the 480-bp upstream sequence, and the 221-bp 3' untranslated region, was amplified by polymerase chain reaction (PCR) using 5'-TCCAAAATATAGAACGAATAAATATC-3' (SEQ ID No: 4) and 5'-AAACGCTATATGAGAACTATTGAAAAGG-3' (SEQ ID No: 5) as primers. Genomic DNA prepared from H4939-1b wild-type strain was used as template. A PCR product was cloned into the YCplac111 vector that had been digested with SmaI and dephosphorylated. Restriction and sequencing analyses confirmed the identity of the cloned CDC5 gene. The introduction of a single copy of a CDC5 fully complemented the defect associated with the cdc5-1 mutation. To generate a galactose-inducible CDC5 construct, YCplac111-CDC5 was digested with DsaI and EcoRI (present in the polylinker of YCplac111 vector). A 2.4-kb fragment was isolated, end-filled, and cloned into YCplac111-GAL1 digested with XbaI, end-filled, and dephosphorylated. The resulting construct contains 41 bp of endogenous CDC5 promoter sequence downstream of the GAL1 promoter.

Immunoprecipitation and kinase assays.

Recombinant Plk proteins expressed in Sf9 cells and yeast cells were N-terminally tagged with hemagglutinin (HA) epitope (HA-Plk; Lee, K. S., et al., 1995, *Mol Cell Biol* 15:7143–7151), and were immunoprecipitated by an affinity-purified anti-Plk antibody against C-terminal 13 amino acid residues (Lee, K. S., et al., 1995, *Mol Cell Biol* 15:7143–7151) or by a monoclonal 12CA5 antibody against HA epitope peptide. Where indicated, #8847 anti-Plk antibody against N-terminal sequence (Hamanaka, R., M. et al., 1995, *J. Biol. Chem* 270:21086–21091) was used to immunoprecipitate both HA-Plk and HA-PlKΔC proteins from yeast cell lysates.

Yeast cells were lysed in TED buffer (40 mM Tris-Cl (pH 7.5), 0.25 mM EDTA, 1 mM DTT, 1 mM AEBSF (Pefabloc; Boehringer Mannheim, Indianapolis, Ind.), 10 mM/ml pepstatin A, 10 μM/ml leupeptin, and 10 μM/ml aprotinin) with an equal volume of glass beads (Sigma). Lysates were spun at 2000 g for 2 min to remove unbroken cells and beads. Supernatants were subjected to further centrifugation at 15,000 g for 30 min to clarify heavy cellular materials. The resulting supernatants (S15) were diluted to 1 ml with TBSN buffer (20 mM Tris-Cl (pH8.0), 150 mM NaCl, 0.5% NP-40, 5 mM EGTA, 1.5 mM EDTA, 0.5 mM Na$_3$VO$_4$, and 20 mM p-nitrophenyl phosphate (PNPP) supplemented with protease inhibitors, then incubated with antibodies. Protein A-Sepharose 4B (Zymed, San Francisco, Calif.) was added and incubated for an additional 1 hr to precipitate the antibodies.

For measuring the kinase activity of Plk, assays were carried out in a kinase cocktail (TBMD: 50 mM Tris-Cl (pH 7.5), 10 mM MgCl$_2$, 5 mM DTT, 2 mM EGTA, 0.5 mM Na$_3$VO$_4$, and 20 mM PNPP) supplemented with 3 μg of dephosphorylated casein (Sigma) and 25 μM ATP (5 μCi of γ$^{-32}$P-ATP; 1Ci=37 Gbq) in assays of mammalian Plk kinase, and 4 μg of dephosphorylated casein (Sigma) and 10 μM ATP (10 μCi of γ$^{-32}$P-ATP) in assays of yeast Cdc5 kinase. Where indicated, purified tubulin was used as substrate.

Western blot analyses.

Western analyses were carried out using affinity-purified Plk antibody, HA antibody, or anti-EGFP (Clontech, Palo Alto, Calif.) at a concentration of 0.5 μg/ml. Proteins that interact with antibodies were detected by the enhanced chemiluminescene (ECL) western detection system (Amersham, Arlington Heights, Ill.).

Flow cytometry analyses.

To induce the expression of Plk, transformants were cultured in YEP-galactose as described above, and cells were harvested at the indicated time points. After washing twice with H$_2$O, cells were fixed with 70% ethanol, then treated with RNAse A (1 mg/ml) in PBS for 30 min at 37° C. After disrupting the cells for 1 min with a sonicator (model W-375; Heat systems-Ultrasonics Inc., Plainview, N.Y.), cells were stained with propidium iodide (50 μg/ml) in PBS. Flow cytometry analyses were performed with a Cellquest program (Becton Dickinson, San Jose, Calif.).

Cell staining and immunofluorescence microscopy.

Yeast transformants were cultured in YEP-galactose to induce the expression of Plk proteins as described above. Formaldehyde was added directly to culture medium to a final concentration of 3.7%, mixed and allowed to fix for 2 hrs. Cells were washed twice with PBS and were subjected to various stainings.

Indirect immunofluorescence was performed as described previously (Pringle, J. R., 1991, *Methods in Enzymol* 194:732–735). To visualize bud scars and other cell wall chitin patches, cells were stained with 0.01% of calcofluor (Fluorescent Brightener 28; Sigma) for 5 min. Fluorescence microscopy was performed using a Nikon Microphot SA microscope with a 63× Plan-apo objective.

To visualize the neck filament-associated septin ring structures, immunolocalization for Cdc10 (Kim, H. B., et al., 1991, *J Cell. Biol.* 112:535–544; Slater, M. L., et al., 1985, *J. Bacteriol.* 162:763–767) was carried out. Briefly, cells obtained as above were treated for 30 min with 200 μg/ml of zymolyase-20T (ICN Immunobiologicals, Irvine, Calif.) in a buffer containing 1.2 M sorbitol, 40 mM potassium phosphate (pH 6.5), and 0.5 mM MgCl$_2$, then washed and resuspended in PBS supplemented with 0.1% bovine serum albumin (BSA; Sigma Corp., St. Louis, Mo.). Affinity purified rabbit polyclonal antibody against Cdc10 was used at 1:250 dilution. FITC-conjugated goat anti-rabbit IgG (Jackson Immunoresearch Laboratories, West Grove, Pa.) was used at 1:200 dilution. Alternatively, rhodamine-corjugated goat-anti rabbit IgG (Zymed Laboratories, Inc., Calif.) was used.

To visualize DNA, either 40 μg/ml of propidium iodide (Sigma) or 2.5 μg/ml of 4',6-diamidino-2-phenylindole dihydrochloride (DAPI; Calbiochem, San Diego, Calif.) was added before washing the secondary antibody with PBS containing 0.1% BSA. Stained cells were viewed under a Zeiss LSM410 confocal microscope equipped with a Krypton/Argon laser.

Microtubules were visualized using YOL1/34 rat anti-tubulin antibody (Accurate Chemical and Scientific Corp., N.Y.) and goat anti-rat CY3 antibody (Jackson ImmunoResearch Laboratories, Inc., Pa.). Actin was localized using rhodamine-conjugated phalloidin (Molecular Probe, Oreg.). Confocal fluorescent images were collected with a Bio-Rad MRC 1024 confocal scan head mounted on a Nikon Optiphot microscope with a 60× planapochromat lens. Each image is the Kalman-averaged product of approximately 4 scans generated by using LaserSharp software.

Example 1

In vitro Kinase Activity of Plk Mutant Protein Expressed in Sf9 Cells: Construction of T210 Mutations Members of the polo subfamily were found to have Glu (E206 in Plk) (SEQ ID No:26) and Thr (T210 in Plk) (SEQ ID No:26) at homologous sites (FIG. 1). To analyze the role of residues such as T210 that might be required for Plk enzymatic activity, various mutations were introduced into DNA encoding a murine PLK cDNA. Murine and human Plk genes are 88% identical (Clay, F. J. et al., 1993, *Proc.Natl.Acad.Sci. USA* 90:4882–4886; Hamaka, R. et al., 1994, *Cell Growth Different.*5:249–257), thus structure/function analyses of the murine Plk gene can be generalized to extend to the human and other mammalian polo kinase proteins.

Mutant Plk proteins were expressed in Sf9 cells, immunoprecipitated, and subjected to immune complex kinase assays. Mutation of Plk Thr210 to Asp (T210D) (SEQ ID No:26) increased four fold the in vitro kinase activity of Plk, assayed using casein as substrate. Mutation of Plk Thr210 to Glu (T210E) increased kinase activity marginally, compared to the wild type. In contrast, mutation of Thr210 to Val (T210V) decreased Plk activity three fold (FIG. 2A). These data indicate that Thr210 plays an important role for Plk activity, and that a substitution mutant of Thr210 with a negatively charged amino acid residue can retain the kinase function.

The immediate upstream acidic residue Glu206 present in the Plk wild-type sequence was examined. Mutation of Glu206 to Val (E206V), but not to Asp (E206D), decreased Plk activity three fold, suggesting the importance of a negatively charged residue at this position. Moreover, double mutant E206V T210V showed much less activity than either single mutant E206V or T210V (FIG. 2A), indicating that both Glu206 and Thr210 are required for the kinase activity of Plk.

Replacement of Plk Asp194 with Asn or with Arg (D194N or D194R) (SEQ ID No:26) abolished the kinase activity (FIG. 2A). Wild-type Plk with the C-terminal domain deleted (PlkΔC), which includes deletion of the polo-box (SEQ ID No:2), possessed three-fold increased kinase activity when expressed in Sf9 cells (FIG. 2B). These mutations provide test strains and controls in the Examples herein, and help define the fine structure of the polo kinase and polo gene. These data also show that regulatory signals are found in the Plk gene.

Example 2

Mammalian Plk complements the phenotypic defects associated with *S. cerevisiae* cdc5-1

CDC5 is unique in the genome of *S. cerevisiae* since no other sequences related to the polo box have been found in the Saccharomyces Genome Database (Stanford Univ., CA). In contrast to the presence of multiple Plk-related kinases in mammalian cells. Thus, yeast is particularly suitable as a host for study of the function of the mammalian gene Plk, since the likelihood of non-specific effects that can interfere with measurements of expression of Plk mutant function is diminished in a yeast cell.

Plk mutants were expressed in yeast under the GAL1 promoter to determine whether wild-type or mutationally activated Plk was able to complement the defect associated with the cdc5-1 mutation, and whether expression of Plk mutants influences aspects of the cell cycle, cytoskeleton structures, or cell morphology. Plk WT and mutant proteins were conditionally expressed under the control of the GAL1 promoter, such that Plk protein was expressed in YEP-galactose medium, but not in YEP-glucose medium. To examine whether Plk complements the defect associated with the cdc5-1 mutation, cells were transformed with various YCplac111l-GAL1-HA-PLK mutant constructs and transformants were selected on synthetic minimal medium plates lacking leucine, and were streaked on YEP-glucose or YEP-galactose plates and incubated for 3 days.

As a comparison, the cdc5-1 mutant cells were also transformed with YCplac111-CDC5, which expresses the yeast wild-type Cdc5 under control of the endogenous promoter. Expression of each of Plk WT (SEQ ID No:26) and mutant T210D genes was observed to complement the cell division defect of the cdc5-1 mutant to a similar extent as cells having the wild-type endogenous Cdc5 gene, whereas each of mutant K82M (inactive form of Plk due to the mutation of the Lys82 in the ATP binding motif to Met), mutant D194N, and mutant D194R did not (FIG. 3A). However, the C-terminally deleted PlKΔC and double mutant T210DΔC complemented the cdc5-1 defect to a lesser extent than the full-length forms.

To quantitatively determine the complementation capability of Plk towards the cdc5-1 defect, analysis of doubling time, cell cycle profile, and cell volume changes upon expression of various Plk mutants were performed with cells grown at 37° C. in YEP-galactose medium. Under these conditions, the cdc5-1 mutant grew marginally, while the cdc5-1 mutant transformed with YCplac111-CDC5 grew with a doubling time of 3.5 hrs. Expression of either of the Plk wild-type (SEQ ID No:26) or mutant T210D gene completely restored cell doubling time to that of cells expressing endogenous Cdc5, whereas expression of each of mutant K82M, D194N, or D194R did not. Data herein show that expression of Plk active forms (Plk and T210D) are thus capable of fully complementing the cell division defect associated with the cdc5-1 mutation, as determined from the growth rates.

To examine further whether the cell cycle defect observed in the cdc5-1 mutant was also restored by Plk expression, flow cytometric analyses were performed for various cdc5-1 transformants cultured at 37° C. in YEP-galactose medium. Data in FIG. 3B show that the majority of the cdc5-1 mutant cells transformed with the vector control were observed to have arrested when cells had achieved a 2N DNA content (after DNA replication). However, the introduction of YCplac111-CDC5 gene was found to complement the cdc5-1 cell division defect, resulting in the regeneration of 1N DNA-containing populations (peak of cells on the left). Expression of Plk WT (SEQ ID No:26) or T210D also restored this defect of arrest of 2N cells (FIG. 3B), whereas K82M, D194N, or D194R did not. At the restrictive temperature, the cdc5-1 mutant cells showed an enlarged and elongated cell morphology. This mutant phenotype also was completely reversed in the transformants carrying Plk WT or T210D, but not K82M, D194N, or D194R, as determined by the profile of cell volume determined by flow cytometry analyses.

TABLE 1

Enrichment of unbudded cells by elevated Plk activity[a]

(%) cells

| plasmid | | | | | | |
|---|---|---|---|---|---|---|
| vector | 58.0 | 25.8 | 4.3 | 11.9 | | 0 |
| K82M | 61.2 | 25.0 | 4.1 | 9.7 | | 0 |
| WT | 64.5 | 23.4 | 2.6 | 9.5 | | 0 |
| T210D | 71.3 | 14.3 | 3.1 | 5.4 | | 5.9 |
| K82MΔC | 60.9 | 24.1 | 3.9 | 11.1 | | 0 |
| WTΔC | 74.7 | 16.4 | 3.7 | 5.2 | | 0 |
| T210DΔC | 85.2 | 9.9 | 1.5 | 3.4 | | 0 |

[a]A diploid wild-type strain, 1788, transformed with various Plk mutants was cultured in YEP-galactose at 30° C. for 8 h. Cells were then fixed, stained with DAPI, and counted. More than 1,500 cells were counted for each type of transformant. The cells with elongated buds were present only in the T210D transformants.

Thus, the cdc5-1 phenotypes associated with cell cycle defects were restored to wild type by complementation with mammalian Plk or the Plk T210D mutant.

Example 3

Plk Kinase Activity Correlates with Plk Complementation of the cdc5-1 Defect

To examine whether complementation of the cdc5-1 cell division defect is Plk kinase activity-dependent, the cdc5-1 transformants bearing various YCplac111-GAL1-HA-PLK mutant plasmids were cultured under inducing conditions (with galactose) for 10 hrs and cells were harvested and lysed. Plk immune complex kinase was assayed, in cellular lysates clarified to remove insoluble materials, using casein as substrate.

Casein phosphorylation activities were detected in Plk WT (SEQ ID No:26) and in mutant T210D, but not in the K82M, D194N, and D194R transformants, in agreement with the results obtained from expression in Sf9 cells (see FIG. 2A). The increased Plk kinase activity of the T210D mutant in yeast cells was consistent with the elevated activity of this mutant previously observed in Sf9 cells (see FIG. 2A). It is shown here that the T210D polo box mutation causes constitutive kinase activity.

It is here observed that mutation of Thr210 of Plk (SEQ ID No:26) to Asp caused a four-fold activation of kinase, comparable to that observed at the G2/M boundary of cycling cells. In addition, mutation of Thr210 to Val decreased Plk activity three fold, whereas mutation to Glu slightly increased it. The elevated kinase activity resulting from the Asp substitution at Thr210 indicates that Thr210 is a target site which is phosphorylated in vivo. In other examples of the invention, it was observed that mutation of Thr216 to Asp, Glu, or Val completely abolished the kinase activity. Further mutational analyses revealed that a conserved negatively charged residue, Glu206, is as important as Thr210 for Plk activity. Thus, it is apparent that Glu206 and Thr210 play roles in the regulation of kinase activity of Plk.

A CDC5 null mutation, cdc5-6, converts the Asp222 in the conserved DFG motif in the kinase subdomain VII to an Arg (Kitada, K., 1993, *Mol. Cell. Biol.* 13:4445–4457). Plk (SEQ ID No:26) here mutated at Asp194 to Asn (D194N) or Arg (D194R) was found to be inactive when expressed in Sf9 cells (FIG. 2A) or in yeast. In the cdc5-1 mutant, expression of D194N or D194R inhibited cellular proliferation, whereas the vector control or mutant K82M did not. This phenotype was not observed in a Cdc5 wild-type background. Thus each of D194N and D194R can function as a weak dominant-negative protein which can compete with the kinase activity of cdc5-1, but not that of wild-type Cdc5.

Mammalian Plk and yeast Cdc5 share 51% sequence identity in the catalytic domain, and 57% identity in the polo-box (SEQ ID NOs: 19 and 18 respectively), which is present in the noncatalytic domain at the carboxy terminal end of the protein. When wild-type Plk and various Plk mutants were expressed under the control of the GAL1 promoter, the degree of complementation of the cdc5-1 cell division defect was found to be correlated closely with the kinase activity of Plk measured in vitro. Conversely, two mutationally inactivated Plk mutants, D194N and D194R, functioned as dominant-negative forms in a cdc5-1 mutant, but not in a Cdc5 wild-type background. These data indicate that Plk is a functional homolog of *S. cerevisiae* Cdc5. Plk and Cdc5 are native to organisms separated by great phylogenetic distance, therefore the invention herein of complementation of the cdc5-1 defect by Plk indicates that these proteins are part of a highly conserved general mechanism for driving M-phase progression in eukaryotic cells. Thus information concerning chemical effectors, or concerning other cellular proteins capable of interacting with and modulating a function of a polo kinase such as mammalian Plk, or yeast Cdc5, can provide leads to potential anti-cancer, anti-fungal, anti-protozoan, anti-helminthic, and anti-arthropod agents.

Example 4
Ectopic Expression of Mammalian Plk in a CDC5 Wild-type yeast Background Causes Cells to Accumulate in G1 Phase To study the phenotypes associated with Plk expression in a CDC5 wild-type genetic background, various mutant forms of Plk were expressed under GAL1 control in diploid wild-type yeast strain 1788. It was observed that expression of Plk WT partially inhibited cellular proliferation (FIG. 4A). Even greater inhibition of growth was observed by the expression of Plk mutant T210D, but no inhibition by kinase-inactive K82M was found. Greatest inhibition of proliferation was observed in the presence of C-terminally deleted forms, PlkΔC or T210DΔC. In the case of the T210DΔC transformants, cell doubling time became lengthened gradually upon induction of expression, and the cell density never reached a saturation point even after 41 hrs of culture (FIG. 4A).

Flow cytometry analyses revealed that the reason that the expression of Plk active kinase forms inhibited growth was the accumulation of cells in G1 phase. Accumulation of 1N cells was observed to be even more pronounced with the expression of PlkΔC or T210DΔC (FIG. 4B), and was manifest 8 hr after shifting the cultures to YEP-galactose medium. Similar accumulation of 1N cells was obtained with a haploid wild-type strain, indicating that this effect of Plk is not ploidy-specific. However, accumulation of 1N cells was not observed in a cdc5-1 background at the permissive temperature of 23° C. Thus, the expression of activated forms of Plk in a CDC5 wild-type background resulted in inhibition of cellular proliferation, which correlated closely with accumulation of cells in G1.

To examine the effect of mammalian Plk on cell cycle coupling to cell growth, cells in various budding stages were counted. Results obtained after 10 hrs of growth under inducing conditions show that in wild-type recipient cells transformed with the vector control or mutant, only 58–61% of cells K82M or K82MΔC transformants were unbudded cells. In contrast, cells harboring Plk WT (SEQ ID No:26) or T210D had an increased number of unbudded cells, and an even larger number of cells were observed with transformants carrying C-terminal deletion mutants (Table 1). Thus, the phenotype of accumulation of cells in G1 obtained by expression of various Plk mutants correlated closely with the enrichment of cells having the unbudded morphology.

A surprising observation was the presence of cells with unusually elongated buds among the T210D transformants. About 21% of the budded cells and 41% of the large budded cells (5.9% of the total population) showed this unusual morphology, which was not observed in other Plk transformants.

The expression of Plk WT (SEQ ID No:26) or T210D in a CDC5 wild-type background was here observed to cause accumulation of the cells in G1 phase. Consistent with the increase in the kinase activity observed here, accumulation of cells in G1 was further enhanced by the presence of C-terminally deleted mutations of Plk, indicating that the C-terminus of Plk, which includes a highly conserved polo-box (SEQ ID No:2), is dispensable for the observed G1 accumulation effect (FIG. 4B).

Example 5
The Subcellular Location of Plk Correlates with its Influence in the Cell Cycle To examine whether the observed influence of the Plk mutants on the cell cycle is directly related to the increased kinase activity of Plk, the yeast wild-type 1788 cells harboring various Plk mutants were cultured under inducing conditions for 10 hrs, harvested, lysed, and subjected to centrifugation at 15,000 g for 30 min to sediment cellular materials. The level of various Plk mutant proteins present in the lysates was observed. Kinase-inactive forms were found to be more abundantly expressed than active forms. Both the full-length and the C-terminally deleted forms of Plk were found predominantly in the pellet (P15) fraction from the 15,000 g spin, and were found at low levels in the supernatant (S15) fractions. This indicates that Plk was present in the cell associated with high molecular weight cell structures under these conditions of cell lysis.

To examine the quantity and activity of Plk in the cell at different times in the cell cycle and to correlate Plk with its kinase activity, Plk kinase activity present in the S15 fraction was measured by in vitro immune complex kinase assays. Plk was immunoprecipitated from an equal quantity of protein in each of the cell extracts, and subjected to kinase assays using tubulin as substrate. Plk WT prepared from Sf9 cells phosphorylated purified tubulin 10 fold more efficiently than it phosphorylated casein in vitro, while K82M did not. Elevated Plk activity was found in cells of the T210D transformants in comparison to that of Plk WT. The C-terminally deleted double T210DΔC mutant manifested further increased Plk activity, consistent with the observation made in Sf9 cells. The cell cycle influences here observed with Plk expression correlated closely with increases in the kinase activity. Thus expression of active forms of Plk was inhibitory for cellular proliferation and the increased Plk activity was responsible for the enhancement of G1 accumulation. The amount of various expressed Plk mutant proteins could thus be inversely correlated with Plk specific activity.

Example 6

Plk Expression Induces Multiple Septation Structures

In an unbudded *S. cerevisiae,* a ring of chitin which can be stained by the fluorescent dye calcofluor, forms in the cell wall within which the bud emerges. To investigate cellular morphological phenotypes associated with G1 accumulation and whether Plk expression might induce multiple septal structures, wild-type 1788 cells transformed with various forms of Plk mutant were examined for the distribution of chitin and septin ring components. In vector cells transformed with the vector control, strong calcofluor staining was manifest at the bud neck in the dividing cells. In the case of cells transformed with Plk mutant T210D, about 50% of cells with elongated buds had multiple chitin bands along the long bud projection, a configuration never observed in wild-type cells. No multiple chitin bands were observed in the cells transformed with T210DΔC, even though its kinase activity is higher than that of T210D.

Because multiple bands of chitin were observed in the T210D transformants, the distribution patterns of a septin component, Cdc10 (Slater, M. L., et al., 1985, *J. Bacteriol.* 162:763–767) were investigated. In the control cells transformed with vector or K82M, only one septin ring structure was manifest at the bud neck. However, among the long-budded cells observed in T210D transformants, two or more septin ring structures were observed. This phenotype was more pronounced in cells transformed with YEplac111-GAL1-HA-PlkT210D, which replicates in multiple copies per cell. Among cells with elongated buds, greater than 50% showed multiple septal structures. Two distantly placed septin rings were observed in a cell with one nucleus or two already divided nuclei. The extra septin ring was placed either between the two divided nuclei or on the other side of a nucleus present in the long bud. Often, several septin ring structures along the elongated bud were evident in dividing cells having two nuclei. In other long-budded cells, additional septin rings were weakly stainable or less distinct and were sometimes detected as punctuate signals along the elongated bud. No additional septin ring structures were observed in the

TABLE 2

Requirement ot the polo-box and kinase activity of Plk for the induction of an abnormally elongated bud phenotype.*

| | % of cells with abnormally elongated cells | | | | | |
|---|---|---|---|---|---|---|
| plasmids | vector #1 | K82M | WT | T210D | T210D/ W414F | K82M/ T210D |
| vector #2 | 0.0 | 0.0 | 0.0 | 3.4 | 0.0 | 0.0 |
| YCplac33-GAL1-GST-CDC10 | 0.4 | 0.3 | 2.3 | 12.2 | 0.4 | 0.4 |

*A diploid wild-type strain, 1788, co-transformed with various YCp-lac111 GAL1-Plk constructs and YCplac33-GAL1-GST-CDC10 was cultured in YEP + 2% galactose at 30° C. for 12 hrs. More than 1,500 cells were counted for each transformant. Synergistic induction of cells with an elongated bud by co-expression of PlkT210D and GST-Cdc10 was abolished by either the W414F mutation in the polo-box or the K82M mutation in the ATP binding site. Data shown represent the average of two independentexperiments.

cells transformed with T210DDΔC.

*S. cerevisiae* displays pronounced cellular asymmetry during its normal growth and division in production of a daughter cell bud. As a cell initiates the division cycle, polarized cell growth begins with an intrinsic spatial cue, established by cortical actin or septin cytoskeleton proteins. In a CDC5 wild-type genetic background, expression of Plk mutant T210D induced the appearance of cells having elongated buds. Further, these cells were not present in the T210DΔC transformants. Formation of multiple septin ring structures was observed in the T210D transformants, but not in cells carrying T210DΔC. Thus the presence of the C-terminal domain of Plk was here found to be important for regulation of the normal polarized cell growth associated with regulating cortical actin and septin cytoskeleton assembly.

Example 7

Flow-cytometric Detection of Complementation of cdc5-1 by Wild-type but not by Polo Box Mutants of Murine Plk Flow cytometric analyses of cells with a cdc5-1 mutation showed accumulation of cells with 2N (G2/M) DNA content and diminishing of those with 1N (G1) in the population (FIG. 6A). Expression of the wild-type Plk gene, but not the kinase-inactive PlkK82M, complemented the cell division cycle defect of the cdc5-1 mutants, regenerating the 1N DNA-containing population to a similar extent as expression of the wild-type yeast CDC5 gene, as shown in FIGS. 6B, 6C and 6D.

In this example, further analyses demonstrate the role of the polo-box (SEQ ID No:2) in functional complementation of the cdc5-1 defect by Plk expression. That the polo-box is required for capacity of Plk to complement the cdc5-1 defect is shown with a Plk mutation lacking residues 356–604 of the carboxy terminal domain (PlkΔC), which includes the polo-box from amino acid residues 410–439 in Plk (FIG. 5A). The PlkΔC mutation did not complement the cdc5-1 defect (FIG. 6E), despite the fact that expression of the mutation caused a three- to four-fold increase in specific kinase activity, as shown in Examples supra.

To examine specifically whether Plk requires the polo-box (SEQ ID No:2) to complement the cdc5-1 defect, eleven single point mutations were generated in the polo-box, as shown in FIG. 5B and Examples supra. The ability of these mutants to complement the cdc5-1 defect was analyzed by flow cytometry, as shown in Examples supra. No Plk complementation of the cdc5-1 defect was observed with the W414F mutation (FIG. 6F). Plk mutations V415A, L427A and N437D also failed to complement Cdc5. The expression level and kinase activity of the W414F mutant were not affected (FIG. 7, FIGS. 8A and 8B). These results indicate that the presence of the polo-box is required complementation of the cdc5-1 defect.

Example 8
Sequence of the cdc5-1 Mutation

To locate the genetic defect in the cdc5-1 allele, yeast genomic DNA was prepared from each of the cdc5-1 mutant (H5C1A1) and its parental wild-type strain (H4939-1b), and each DNA preparation was used as a template to amplify the full-length cdc5-1 mutant and wild-type CDCS genes, respectively, using the polymerase chain reaction. Restriction and complementation analyses confirmed the identity of the cloned genes.

Sequencing of the cloned genes revealed a point mutation (conversion of Pro511 to Leu) in the cdc5-1 allele. Further, substitution of the P511 L mutation into the wild-type Cdc5 gene abolished ability of the gene to complement the cdc5-1 defect. Consistent with the role of the polo-box domain was the finding that the cdc5-1 allele possessed a single point mutation at the upstream boundary of the polo-box (SEQ ID No:3) (FIG. 8B) that alters the structural integrity and function of this region of the protein.

Example 9
The Effect of Mutations of the Plk Polo Gene on Cell Morphology

Microscopic observation revealed that the majority of cdc5-1 mutant cells grown at the restrictive temperature were greatly enlarged, with heterogeneous cell sizes and shapes observed in the cell population. In forward scatter, this phenotype was observed as a broad, spread out pattern (FIG. 6G). Expression of the wild-type yeast gene Cdc5 (FIG. 6H) or of wild-type mammalian gene Plk, but not that of the kinase-inactive K82M mutant, in cdc5-1 cells successfully complemented this mutation and restored the uniform wild-type cell morphology phenotype (FIGS. 6I and 6J).

Neither Plk mutant W414F nor PlkΔC conferred the wild-type cell morphology (FIGS. 6K and 6L), consistent with the inability of these mutants to rescue growth at the restrictive temperature or to relieve the cdc5-1 cell cycle arrest phenotype.

The results demonstrate the necessity of the presence of both the sequences encoding the kinase activity and the polo-box (SEQ ID No:3) for the ability of Plk to successfully complement the cdc5-1 defect.

Example 10
The Role of the Plk Polo Gene in Cytokinesis

Ectopic expression of the constitutively active Plk T210D mutant gene in an otherwise wild-type genetic background induced production of cells with unusually elongated buds, indicating that polar bud growth was deregulated in these cells. These buds were found to possess ectopic, nascent sites of cytokinesis, as indicated by the localization of Cdc10, one of four essential yeast septins, as rings within these buds.

Expression of the carboxy terminal deletion mutant (PlkΔC) did not induce the phenotype of elongated buds, despite its increased kinase activity, as shown herein, and production of cells having the elongated bud morphology was found to be completely abolished by introduction of a second mutation, the polo box (SEQ ID No:2) defect W414F, into PlkT210D (Table 2). This shows that the polo-box is a key element in regulating cortical actin and septin cytoskeleton assembly.

To investigate the role of septins in the induction of the elongated bud morphology, wild-type cells were transformed with Plk mutant constructs described herein, and with GST-fused CDC10 (GST is glutathione-S-transferase, the fusion used for rapid purification of protein; see Ausubel, F. et al, Eds. "Short Protocols in Molecular Biology", 3rd Ed., 1995, New York:Wiley). GST-Cdc10 expressed under the GAL1 promoter did not induce a significant percentage of elongated buds. However, when GST-Cdc10 was co-expressed with the PlkT210D mutant, the frequency of observed cells having the elongated bud phenotype was synergistically enhanced from 3.4% to 12.2% (Table 2). Cells co-expressing non-fused forms of the Cdc10 and PlkT210D genes showed similar results. Introduction of either the W414F or the K82M mutation into the PlkT210D gene abolished both the PlkT210D phenotype of induction of abnormally elongated buds and the even greater induction by co-expression with GST-Cdc10 (Table 2).

These data show that Plk cooperates with septin proteins to induce this abnormal bud phenotype, and that both the polo-box (SEQ ID No:2) domain and the kinase activity of Plk are required for the induction and regulation of bud growth and cytokinesis.

Example 11
Analysis of in vivo Plk and cdc10 Expression and Activity in Different Genetic To determine whether the abnormal morphology is due to differences either in Plk or Cdc10 expression levels or kinase activities among the various Plk transformants, Western analysis and kinase assays of cell extracts were performed using the methods of the Examples above. The expression of the wild-type and mutant forms of Plk were not affected by co-expression of the GST-Cdc10 gene (FIG. 8A). Wild-type Plk and the PlkW414F mutant exhibited similar levels of enzymatic activity, whereas the activity of PlkT210D was several-fold higher (FIG. 8B). Co-expression of GST-Cdc10 with wild-type or mutant forms of Plk did not significantly affect the kinase activities.

These data indicate that the abrogation of the elongated bud phenotype observed with PlkT210D/W414F expression is due specifically to impairment of the function of the polo-box (SEQ ID No:2) by ithe W414F mutation.

Example 12
Investigation of Plk Location Using Green Fluorescent Protein (GFP) Fusion Constructs Demonstration of inability of the W414F mutant either to complement the cdc5-1 defect or to induce the elongated bud phenotype has been shown herein. Without being bound by any particular theory, a further embodiment of the invention concerns function of the role of polo-box (SEQ ID No:2) in targeting Plk to particular subcellular locations or in mediating the interaction of Plk with an essential substrate or binding protein such as a regulatory or structural protein.

For these determinations, Cdc10 was localized using affinity-purified rabbit polyclonal anti-Cdc10 antibody and rhodamine-conjugated goat anti-rabbit IgG (Zymed Laboratories Inc., CA). Microtubules were visualized using YOL1/34 rat anti-tubulin antibody (Accurate Chemical and Scientific Corp., NY) and goat anti-rat CY3 antibody (Jackson Immunoresearch Laboratories, PA). Actin was localized using rhodamine-conjugated phalloidin (Molecular Probe, OR). DNA was visualized using propidium iodide staining at 40 μg/ml. Stained cells were viewed under a Zeiss LSM410 confocal microscope equipped with a Krypton/Argon laser.

The cellular localization of Plk was investigated using constructs that fuse alleles of this gene to the enhanced green fluorescent protein (EGFP) gene, such that the fusion can then be expressed under the GAL1 promoter. Ycplac111-GAL1-EGFP-PLK fusion constructs were generated by inserting a 700-bp Xho I fragment of the EGFP coding sequence into the Xho I site present at the N-terminal PLK coding sequence. The EGFP coding sequence was amplified by polymerase chain reaction using the pEGFP-N1 plasmid (Clontech Laboratories, Inc., CA) as a template.

Observations indicated that in cells grown at the restrictive temperature, EGFP-fused wild-type Plk and PlkT210D were found to complement the cdc5-1 growth defect to a similar extent as the parental unfused forms. Further, the W414F polo-box mutation substantially eliminated the capacity of EGFP-Plk to complement the cdc5-1 growth defect, and the carboxy terminal deletion mutation abolished complementation completely. These results show that the EGFP-Plk fusion proteins function in the same manner as their non-fusion counterparts.

Ectopic expression of both wild-type Plk (SEQ ID No:26) and PlkT210D EGFP fusion genes in yeast cells yielded two distinct green fluorescent dots in the cytoplasm as well as either one or two bright bands at the bud neck in budded cells. Subsequent immunostaining of cells with antibodies against either tubulin or Cdc10 using a contrasting color revealed that the two dots of staining represented the poles of the mitotic spindle. Further, the bands corresponded to the cytokinesis-associated septin rings. The localization of Plk to the subcellular structures was either greatly diminished or absent in cells expressing PlkW414F or the PlkT210D/W414F double mutant. A Plk construct lacking both the kinase and the carboxy terminal domains (Plk-N$^{1-49}$) yielded a diffuse signal.

These results show that the polo-box directs Plk localization to both the spindle poles and the bud-neck filaments, and that residue tryptophan 414 plays a critical role in targeting Plk to these structures. These observations further indicate that the inability of the W414F mutant to complement the cdc5-1 defect and induce the elongated bud phenotype were correlated with the loss of the function conferring localization to specific cellular sites.

Example 13
Localization of Plk at the Multiple Bud-neck and Septal Structures in T210D Mutants Since Plk was shown herein to be localized to the septin ring structures at the bud-neck, the cellular location of Plk at the additional septal structures induced by the expression of PlkT210D was investigated. Immunostaining using the techniques above revealed that PlkT210D (green color) co-localized with Cdc10 (red color) at both the neck filaments and at the additional septal structures. The additional septal structures were observed in many cells as single bands, and distinct double septin ring structures were evident as well (stained both red and green). The same structures in a given cell could be visualized in both red and green. Accumulation of actin was also evident at the neck filaments and at the additional septal structures. The presence of actin in some of the septal structures here indicated that the ectopic septal structures were able to recruit additional proteins into the cytokinetic components.

Thus complementation of the cdc5-1 defect in S. cerevisiae by a mammalian Plk gene required the presence both of the Plk protein kinase activity and the Plk polo-box domain (SEQ ID No:2). The presence of both domains of Plk was also found to be required for Plk-induced deposition of septins in budding yeast. The examples here indicate that the polo-box serves to target the catalytic activity of Plk to the spindle poles, cytokinetic neck filaments, and septal structures. Further, polo kinase play an important role in regulating septal structure formation during cytokinesis.

Example 14
Both the Polo-box and the Kinase Activity of Yeast Cdc5 are Required for Functional Complementation of the cdc5-1 Defect Studies of mammalian polo kinase Plk above provide information correlating the functions of enzyme activity and the polo box (SEQ ID No:2) with the role of Plk in regulating mitosis. These studies provide strains and conditions for cell-based screens for discovery of novel therapeutic agents for a subject having an unwanted cell, in particular, an unwanted mammalian cell such as a cancer cell. Screens can also be devised for use in obtaininng anti-fungal agents. For this embodiment, it is preferable to use a polo kinase of fungal origin, for example from S. cerevisiae or from S. pombe. Examples infra provide data on the structure and function of yeast polo kinase Cdc5.

Whether the yeast polo-box domain (SEQ ID No:3) is required for the function of Cdc5 in addition to the kinase domain was investigated. A mutation analogous to the PlkW414F substitution was introduced into Cdc5. Unlike Plk, the cdc5W517F mutant still possessed a significant capacity to complement the cdc5-1 defect. In mammalian Plk, the V415A or L427A mutations in the polo-box also significantly reduced the ability of Plk to complement the cdc5-1 defect. Thus, two analogous yeast mutations, V518A and L530A, were introduced into cdc5W517F.

It was observed that whereas wild-type Cdc5 rescued the cdc5-1 growth defect, the resulting cdc5 mutant, cdc5W517F/V518A/L530A (indicated as cdc5FAA; FIG. 9), was not able to restore growth to a detectable level, as single colonies were not formed at the restrictive temperature. The N209A mutation in Cdc5, which inactivates its kinase activity, also failed to complement the cdc5-1 defect. Subsequent flow cytometry analyses revealed that, at the restrictive temperature, cells transformed with either cdc5FAA or cdc5N209A arrested largely with a 2N DNA content similar to the DNA profile observed with vector-transformed cells (FIGS. 10A, B, and D). Failure to observe a distinct cell cycle arrest with a 2N DNA content due to an apparent cell lysis which occurs under these conditions, and shown in Examples herein. Wild-type Cdc5, however, restored the cell division cycle defect of the cdc5-1 mutants, regenerating the 1N DNA-containing population (FIG. 10C).

Microscopic observations revealed that, at the restrictive temperature, the cdc5-1 mutant cells transformed with the vector control had become greatly enlarged, with heterogeneous cell sizes and shapes. This phenotype was shown in forward scatter as a peakless, wide-spread pattern (FIG. 10E). It was also apparent that these cells had lost distinct morphology at the cell edges, indicating cell lysis. Expression of wild-type Cdc5 (FIG. 10G), but not the kinase-inactive N209A mutant (FIG. 10F) or the cdc5FAA triple mutant (FIG. 10H), restored the heterogeneously enlarged cell population to uniform wild-type morphology. Taken together, the above data demonstrate the necessity of both the kinase activity and the polo-box (SEQ ID No:3) for normal Cdc5 function, and ability to successfully carry out mitosis and cell division.

Example 15
The FAA Mutations in the Yeast Polo-box Abolish Cdc5 Protein Localization at Spindle Poles and Cytokinetic Neck-filaments To examine whether the inability of the FAA mutant to complement the cdc5-1 defect was due to a disrupted localization, the cellular localization of Cdc5 was investigated. An enhanced green fluorescent protein (EGFP) was inserted by genetic fusion at the N-terminus of Cdc5, and the resulting EGFP-Cdc5 fusion protein was expressed under control of the GAL1 promoter. Ectopic expression of each of wild-type Cdc5 and cdc5N209A yielded distinct fluorescent dots in the cytoplasm as well as one bright band, or occasionally one bright and one weak band, at the mother-bud neck. Subsequent immunostaining with anti-tubulin antibody revealed that among the multiple dots observed in some cells, only two were present at each end of the mitotic spindle, suggesting that not all the dots associate with spindle poles. In addition, immunostaining with anti-Cdc10 antibody showed that the observed bands of EGFP-Cdc5 co-localized with the cytokinesis-associated septin rings. In sharp contrast, cdc5FAA failed to localize to either the spindle poles or the cytokinetic neck-filaments. Both Cdc5 wild-type and the FAA mutant weakly stained chromosomal DNA, suggesting that Cdc5 associates also with chromatin structures independent of the polo-box. These data show that the polo-box (SEQ ID No:3) directed Cdc5 localization to the spindle poles and the bud-neck-filaments, and that the FAA triple box mutations disrupted a critical role of the polo-box in targeting Cdc5 to these structures. Thus, inability of the FAA mutant to complement the cdc5-1 defect is due to the loss of its specific cellular localization.

Strong multiple dot signals were evident both in wild-type Cdc5 and in cdc5N209A transformants. However, induction of multiple dot signals did not correlate with kinase activity, since transformants expressing kinase-inactive cdc5N209A showed significantly more cells with multiple dots (19% of the total population [24 cells out of a total of 132] when induced for 12 hrs) than those expressing wild-type Cdc5 (6% of the total population [9 cells out of a total of 149]). Multiple dot signals were most often present in the mother cells (see the NA and WT panels in FIG. 3). Among the 19% (24/132) of the population with multiple dots present in cdc5N209A transformants, 17% of the total (22/132) of the cells possessed multiple dots exclusively in the mother cells, while only a few (2/132) showed exclusively in the daughter cells.

TABLE 3

Requirement of the polo-box and kinase activity of Cdc5 for the induction of an abnormally elongated bud phenotype.*
Vector, YCplac22-GAL1; NA, YCplac22-GAL1-EGFP-Cdc5N209AΔDB; WT, YCplac22-GAL1-EGFP-Cdc5ΔDB; FAA, YCplac22-GAL1-EGFP-Cdc5W517F/V518A/LS30AΔDB.

| plasmids | % of cells with abonormally elongated buds | | | |
|---|---|---|---|---|
| | vector | NA | WT | FAA |
| | 0.0 | 0.1 | 39.0 | 0.0 |

*A diploid wild-type strain, 1788, transformed with various Cdc5 constructs was cultured in YEP-galactose at 30° C. for 12 hrs. More than 1,500 cells were counted for each transformant. Induction of cells with an elongated bud was abolished by either the FAA mutation in the polo-box or the N209A mutation in the kinase domain.

In contrast to the dots, a sharp band was always observed at the daughter side of the mother-bud neck (determined by the shape of the chromosomal DNA stained with propidium iodide and the co-localization of signals from the anti-Cdc10 staining). Closer examination revealed that a much weaker band was also present at the mother side of the mother-bud neck, but it was not always detectable. However, the presence of two bands at the mother-bud neck was evident in the transformants expressing a more stable form of Cdc5, cdc5ΔDB, which lacks two putative destruction-boxes at the N-terminus. At times, a ring of fluorescent signal was also observed, indicating that Cdc5 was present as a continuous ring structure at the mother-bud neck.

Example 16
Induction of Additional Septal Structures by Ectopic Expression of Yeast Cdc5.

Expression of the constitutively active mammalian PlkT210D in yeast resulted in induction of a class of cells with abnormally elongated buds possessing additional septin rings (Examples herein). When Cdc5 was expressed for 12 hrs under the control of the GAL1 promoter (pKK507; YCplac22-GAL1-Cdc5), approximately 25% of the cells displayed this abnormal elongated morphology. To investigate whether additional septin ring structures were also formed in these cells, cells were immunostained with anti-Cdc10 antibody.

Observations showed that an additional one to three septal structures were evident within the elongated buds in addition to the septin ring structures at the native cytokinetic neck-filaments. Induction of these multiple septal structures did not correlate with the phase of the cell division cycle, since ectopic septal structures were formed even in the absence of nuclear division. In cells with two divided nuclei, these nascent septal structures were present either between or at one side of the two divided nuclei. These observations indicate that the placement of these structures had occurred independent of the position of the nuclei.

Example 17
Ectopically-expressed Cdc5 Localizes at Additional Cytokinetic Septal Structures Because Cdc5 localized at endogenous cytokinetic neck-filaments, and could induce multiple septal structures within the elongated buds, the association of Cdc5 itself with the ectopic septal structures was investigated. It was observed that overexpression of EGFP-Cdc5 yielded additional distinct fluorescent bands within the abnormally elongated buds (data not shown). To enhance the localization of Cdc5 at additional septal sites, an N-terminally truncated form of EGFP-Cdc5, EGFP-cdc5ΔDB, which has lost its N-terminal 66 amino acid residues, was used. Deletion of this N-terminal sequence, which contains two putative destruction boxes (Shirayama, M. et al., 1998, *EMBO J.* 17:1336–1349), resulted in a five- to ten-fold increase in protein level. At the restrictive temperature, galactose-induced expression of EGFP-cdc5ΔDB, but not of EGFP-cdc5FAAΔDB or EGFP-cdc5N209AΔDB, functionally complemented both the cell growth and the cell cycle defects associated with the cdc5-1 mutation.

The truncated cdc5 fusion proteins also gave the same localization patterns as their parental full-length Cdc5 proteins, indicating that deletion of the N-terminal 66 amino acid residues did not affect the subcellular localization or functions of these Cdc5 constructs. As with full-length Cdc5 (pKK507), expression of EGFP-cdc5ΔDB, but not of the FAAΔDB or N209AΔDB mutant, induced cells with abnormally elongated buds (see infra). Further, expression of EGFP-cdc5ΔDB yielded more intense fluorescent bands within the elongated buds, reflecting the iabundance of the protein in comparison to full-length EGFP-Cdc5. The additional septal structures were seen as either single or double bands.

Thus, immunolocalization studies with an anti-Cdc10 antibody to investigate whether the additional bands observed with EGFP-cdc5ΔDB co-localized with the ectopic septin ring structures previously observed with Cdc5 overexpression showed that cdc5ΔDB co-localized with Cdc10 at both the native neck-filaments and the additional septal structures; however, in the elongated cells, localization of both Cdc5 and Cdc10 at the bud neck-filaments was weaker than at the ectopic sites.

In order to examine whether actin was recruited to the additional septal structures, subsequent staining was carried out with rhodamine-conjugated phalloidin. Actin was observed to accumulate at both the native neck-filaments and the ectopic septal structures. However, not all additional septal structures accumulated actin, probably because actin polarization at cytokinetic filaments occurs only during cytokinesis. The presence of actin at the ectopic septal structures indicates that the yeast polo kinase Cdc5 was sufficient to recruit additional cytokinetic components to these sites.

These data indicate that yeast polo kinase Cdc5 itself is targeted to ectopic, nascent septation sites, and that Cdc5, like mammalian Plk, plays a major role in induction of cytokinetic events.

Example 18

Both the Polo-box and the Kinase Activity of Cdc5 are required to induce Abnormally Elongated Buds The ability of galactose-driven expression of Cdc5 to induce with unusually elongated buds indicated that polar bud growth had been deregulated. This phenotype was enhanced with expression of the more stable protein, EGFP-cdc5ΔDB. Cells with unusually elongated buds were evident as early as 6 hrs after induction. After 12 hrs of induction, 39% of the cells possessed distinctly elongated buds.

In sharp contrast with EGFP-cdc5ΔDB, the introduction of either the FAA mutations in the polo-box or the N209A mutation that inactivates the kinase abolished the capacity of EGFP-cdc5ΔDB to induce this phenotype (Table 3). These data indicate that ectopic expression of Cdc5 induced an abnormally elongated bud phenotype, and that both the polo-box domain and the kinase activity of Cdc5 are required for this event.

Example 19

The FAA Mutations in the Yeast Polo-box do not Affect Expression Level or Kinase Activity of the Yeast Cdc5 Protein It is possible that inability of EGFP-cdc5FAAΔDB to induce abnormally elongated buds or to localize at the cytokinetic septal structures could be due to alteration of expression or kinase activity of Cdc5. In cellular lysates prepared after inducing for 12 hrs, both the wild-type and the FAA mutant proteins were present at similar levels, whereas the kinase-inactive cdc5N209AΔDB was two- to three-fold more abundant. In vitro kinase assays showed that both EGFP-cdc5ΔDB and EGFP-cdc5FAAΔDB exhibited similar levels of both autophosphorylation and casein phosphorylation enzyme activities, whereas EGFP-cdc5N209AΔDB had no detectable activity (FIG. 7B, top panel). Western analyses revealed that approximately equal amounts of EGFP-cdc5N209AΔDB, EGFP-cdc5ΔDB, and EGFP-cdc5FAAΔDB proteins were precipitated.

These data indicate that abrogation of the elongated bud phenotype observed with EGFP-cdc5FAAΔDB yeast mutant expression was specifically due to disrupted function of the yeast polo-box (SEQ ID No:3) by the FAA mutations, and not to altered expression of kinase activity.

Example 20

The Introduction of the FAA Mutations in the Polo-box Abolishes Inhibition of Cytokinesis by the Carboxy Terminal Domain of Cdc5

The FAA mutations in the polo-box (SEQ ID NO:13) domain abolished the localization and function of Cdc5, showing that the polo-box functions as an essential interaction domain to target the catalytic activity of yeast Cdc5 to specific subcellular locations. Thus, without being bound by any particular theory, ectopic expression of the polo-box domain could lead to inhibition of Cdc5 function by competing for an essential binding protein(s), a "polo kinase binding protein peptide" or (PKBPP) that interacts with endogenous Cdc5. To test this possibility directly, both the wild-type and the FAA mutant forms of the carboxy terminal domain of Cdc5 (these constructs are deleted of amino acids 6 to 239) were expressed as HA-EGFP-fusion proteins (HA-EGFP-cdc5.C-term). Expression of the HA-EGFP-cdc5.C-term peptide induced about 10% of the total population to form chains of connected cells. These cells appeared to be different from the cells with elongated buds induced by expression of Cdc5 or Plk in that the cells in chains showed normal sizes and morphologies. Strikingly, this phenotype was completely abolished by the introduction of the FAA mutations into the polo-box.

Expression of the HA-EGFP-cdc5.C-term peptide yielded multiple dots in the cytoplasm and strong bands at the mother-bud neck, whereas its FAA mutant yielded only diffuse signals. Immunostaining with anti-Cdc10 and anti-tubulin antibodies revealed that, as with full-length Cdc5, the carboxy terminal peptide localized to the cytokinetic neck-filaments and spindle poles. A much smaller construct lacking the entire N-terminal kinase domain (amino acids 6 to 448) also localized to these sites and induced a similar phenotype, whereas its FAA mutant did not. This observation indicates that the carboxy terminal domain of Cdc5 is sufficient to localize to the neck-filaments, and that an intact polo-box (SEQ ID No:3) is required for this event. In total cellular lysates, both HA-EGFP-cdc5.C-term and its FAA mutant were expressed at similar levels. Thus, the inability of the FAA mutant to localize at specific subcellular locations and induce chains of connected cells is apparently due to the loss of the function of the polo-box.

The observed chains of cells may result from a failure either in cytokinesis or in cell separation after cytokinesis. To distinguish between these two possibilities, these cells were digested with zymolyase and examined to determine whether they dissociated from one another after cell wall digestion. Microscopic examination reveealed cells remained connected after this treatment, or this treatment followed by sonication, to a similar extent. In addition, nuclei were present in most of the buds in the connected cells.

These data strongly indicate that the chains of cells share cytoplasm as a single cell, and that normal nuclear divisions occurred without the normal cytokinesis events. Taken together, the results indicate that expression of the carboxy terminal domain of Cdc5, but not the FAA mutant, results in the inhibition of cytokinesis.

Growth of these cells is severely retarded, as determined from very small colony size and slow doubling rate. These data indicate that introduction of all or a portion of a carboxy terminal of a polo kinase carrying a functional polo box can inhibit the growth of that cell, and that the functional portion can serve as a template for design of synthetic chemicals that mimic the effect of the carboxy terminal.

Example 21

Identification of Additional Polo Boxes PB2 and PB3

The original definition of the polo-box (SEQ ID No:2) from Examples supra includes sequences 410–439. The sequence alignment of the entire carboxy termini of four polo kinases is given in FIG. 10. Examination of conserved residue shows that there are at least two other regions that are likely to be important in the M-phase specific localization functions determined by the carboxy terminal of the polo kinase. These additional polo boxes are designated polo-box 2 and 3 (PB2, the consensus sequence of which is also given in SEQ ID NO:6, and the consensus sequence of which is also given in PB3, SEQ ID NO:7).

Example 22
Method for Identification of Plk Interacting Proteins with Two-hybrid Screens Using Full-length, Wild-type, or W414F Carboxy Terminal as Bait Plk polo-box (SEQ ID No:2) directs localization of cellular proteins that interact specifically with wild-type, but not polo-box mutant protein, to various mitosis- and cell division-related structures. Because of these properties, the polo box serves to regulate and coordinate events in and around M phase. Because such processes present an excellent target for therapeutic interference in growth of an unwanted eukaryotic cell in a subject, this invention utilized the yeast two-hybrid screen to obtain a collection of additional proteins or peptides thereof that interact with a polo kinase (indicated as a polo kinase binding partner peptide, PKBPP).

Using the terminology of the two-hybrid system (Vojtek et al., 1993), vectors were engineered to have Plk carboxy terminal constructs as bait (see FIG. 11) and a mouse embryo 9.5/10.5-day cDNA library as prey. (A different strategy was used to identify TCTP/p23, i.e., full length Plk and a cDNA library from HeLa cells with inserts of 1–2 kb in the Examples, infra).

The mouse library was constructed to express size-limited protein sequences as cDNA inserts that were size-selected for a range of between 350–700 bp. Such screens can detect specific peptides large enough to include modules that interact with the polo-box, and further, all domains of a potential interacting protein can be present in qunatities of similar abundance. A summary of the baits used in the screen is given in FIG. 11.

The two-hybrid screen was employed to obtain several surprising PKBPs as shown in Examples below.

Example 23
GRASP65 Isolated by Interaction with Plk Residues 1–400 is a PKBPB

GRASP65 (SEQ ID NO:24) (Golgi Reassembly Stacking Protein, amino acid residues 6–114) was isolated as a peptide that interacted with Plk 1–400 as the bait (FIG. 12). This portion of Plk includes the catalytic domain and a portion of the carboxy terminal but not the polo box. Further, the same GRASP65 cloned sequences were isolated in an independent screen with Plk 323–499 in a polo box-dependent fashion, i.e., use of Plk mutant W414F did not yield this signal.

GRASP65 (SEQ ID NO:24) is a Golgi-associated protein that, together with its binding partner GM130, becomes phosphorylated during fragmentation and disappearance of the Golgi in the mitosis phase. Upon stacking of the Golgi after mitosis, these proteins are dephosphorylated (Barr, F. et al., 1998, *EMBO J.* 17:3258–3268; Lowe, M. et al., 1998, *Cell* 95:783–793). Cdc2 kinase phosphorylates GM130, however the protein kinase that phosphorylates GRASP65 during mitosis has not been described.

The data herein indicate that Plk can be a GRASP65 (SEQ ID NO:24) kinase. Further, the ability of Plk to recognize, bind to and enzymatically phosphorylate GRASP65 presents a novel target for screens to identify therapeutic agents to treat a subject having a cancer, a fungal infection, an arthropod infestation, or another unwanted eukaryotic cell.

Example 24
CCT-ε Isolated by Interaction with Plk Residues 323–499

The chaperonin-containing-TCP (CCT) epsilon (SEQ ID NO:25) (amino acid residues 13–139) subunit was isolated using the two-hybrid screen by its ability bind to Plk 323–499 in a polo box-dependent manner (FIG. 13). CCT is a multi-subunit eukaryotic cytoplasmic chaperonin complex comprised of eight subunits. Genetic and biochemical studies show that CCT is involved in the proper protein folding of actin, and α-, β-, and γ-tubulin, and is essential for the organization of the cytoskeleton (Liang, P. et al., 1997, *J. Cell Sci.* 110:1431–1440). Moreover, CCT components have been shown to be associated with the centrosome, and antibody studies suggest it is involved in critical centrosome functions such as microtubule nucleation (Brown, C. et al., 1996, *J. Biol. Chem.*271:824–832).

The interaction shown here of CCT-ε (SEQ ID NO:24) with wild-type but not W414F Plk 323–499 suggests two possibilities for a role for CCT-ε or for the CCT complex in the activity of Plk Without being bound by any particular theory, CCT-ε may be required for correct folding of Plk into a native functional molecule, and in the absence of this activity to bind to and function on the W414F mutant, the unfolded carboxy terminal of Plk may not recognize the centrosome. Alternatively, CCT or CCT-ε may guide Plk to the centrosome after interacting with wild-type Plk C terminal sequences.

Independent of the mechanism by which Plk (SEQ ID No:26) and CCT-ε (SEQ ID No:25) interact after binding, the demonstration herein of the polo box-specific binding of Plk with CCT-ε, showing that CCT-ε is a PKBPP, offers that interaction as a novel target to exploit for screening for a therapeutic agent capable of inhibiting growth of an unwanted eukaryotic cell in a subject.

Example 25
The Final Carboxy Terminal of Plk (Residues 500–603) Interacts with Plk 323–499

The two hybrid method using Plk 323–499 (SEQ ID No:26) as bait enabled isolation of another cDNA encoding a PKBPP capable of binding to this portion of Plk. A cDNA encoding Plk 500–603 (SEQ ID No:26) was isolated, and yielded a signal with Plk 323–499 that depended on the presence of the wild-type polo-box. Further, Plk 450–603 (SEQ ID No:26), when used as a bait, detected a cDNA encoding Plk 350–512 (SEQ ID No:26) in the library.

These unexpected data show that with the W414F mutation, which likely destabilizes the secondary structure of the carboxy terminal, interferes with essential Plk binding functions in the cell. Further, these data indicate that nearly the entire carboxy terminal region of Plk is organized in a fashion required for centrosomal localization, as specific functions were attributed to each subregion throughout the carboxy terminal in the data in the Examples supra.

Example 26
Translationally Controlled Tumor Protein TCTP/23 Binds to Plk and is a Putative Plk Substrate A HeLa cell cDNA library having inserts of 1–2 kb was fused to a GAL4 activation domain, and was screened using full-length Plk fused to a GAL4 DNA-binding domain. Clones of the translationally controlled tumor protein TCTP/p23 (SEQ ID No:27) (Bohm, H. et al., 1991, *Biomed.Biochim.Acta* 50:1193–1203) were observed to constitute a large fraction of the protein-protein interactions that were obtained by this procedure.

TCTP was originally cloned as an abundant mRNA in untranslated RNPs and is a protein of about 23 kDa. No functional studies of TCTP/p23 (SEQ ID No:27) have been reported, hence its role in the cell has been heretofore unknown.

Full-length TCTP/p23 (SEQ ID No:27) cDNA was isolated and cloned into a pGEX vector to produce a GST-fusion protein. Protein produced in insect cells with recombinant baculovirus showed that TCTP/p23 can interacted with HA-Plk but not HA-Snk. Further, TCTP/p23 was found to be a substrate for Plk kinase activity, and was phosphorylated by Plk on serine residues at positions 46 and 64.

To determine whether TCTP/p23 (SEQ ID No:27) is a physiological substrate of Plk, lysates were prepared from a population of mitotic HeLa cells, and were assayed for TCTP/p23 kinase activity. Data show that the mitotic lysates contained 20-fold more activity than those prepared from an unsynchronized randomly growing cell population.

Fractionation over ion-exchange columns showed that the TCTP/p23 kinase activity co-eluted from the columns with Plk. Moreover, the activity identified in cell lysates failed to phosphorylate the S46A, S64A double mutant, supporting the conclusion that TCTP/p23 (SEQ ID No:27) is a physiological substrate of Plk.

TCTP/p23 (SEQ ID No:27) was used as the bait in a two-hybrid screen. Surprisingly, these screens identified four clones that encode proteins present in the 26S proteasome. The 20S proteasome core consists of 7 alpha and 7 beta subunits. TCTP/p23 showed strong interaction with an alpha subunit zeta and a beta subunit HC5 (Coux, O. et al., 1996, *Ann. Rev. Biochem.* 65:801–847). Two ubiquitin-interacting proteins from the 26S subunit were also identified. One is the multi-ubiquitin-chain binding protein (Mcbl/subunit 5a), which binds poly-ubiquitin chains and poly-ubiquitin substrate conjugates (Young, P. et al., 1998, *J. Biol. Chem.* 273:5461–5467), and the other is elongation factor 1δ, which, in addition to being involved in protein synthesis, also acts as a ubiquitin isopeptidase to release ubiquitin from multi-ubiquitin chains and facilitate the entrance of the degradation target into the proteasome pore (Gonen, H. et al., 1994, *Proc. Natl. Acad. Sci. USA* 91: 7648–7652).

Examples using transient expression of GFP-tagged TCTP indicate that overexpression results in cell cycle arrest with fragmented nuclei and 2N DNA content. This phenotype is similar to that observed herein when Plk was overexpressed in animal cells, indicating that TCTP can be a regulator mitotic processes.

In addition to examining the role of the TCTP/p23 (SEQ ID No:27) protein in the cell cycle, the data here show that Plk phosphorylation of TCTP/p23 can serve as a novel target for screens to isolate therapeutic agents to treat a subject having an unwanted eukaryotic cell such as a tumor cell, a fungal cell, or an arthropod cell.

SEQUENCE LISTING

```
<160> NUMBER OF SEQ ID NOS: 27

<210> SEQ ID NO 1
<211> LENGTH: 28
<212> TYPE: PRT
<213> ORGANISM: Artificial Sequence
<220> FEATURE:
<221> NAME/KEY: VARIANT
<222> LOCATION: (517)...(543)
<223> OTHER INFORMATION: Consensus of PB1 polo box sequences from the
      polo kinase proteins of 4 organisms:  Saccharomyces
      cerevisiae; Schizosaccharomyces pombe; Drosophila
      melanogaster; Mus musculus.  The residues labeled
      "Xaa" do not share a consensus among these
<222> LOCATION: refer to
      the location of the consensus sequence in the
      Saccharomyces cerevisiae CDC5 polo kinase gene.
      Xaa=Any amino acid
<223> OTHER INFORMATION: Xaa = Any Amino Acid

<400> SEQUENCE: 1

Lys Trp Val Asp Tyr Ser Xaa Lys Tyr Gly Xaa Gly Tyr Gln Leu Xaa
1               5                   10                  15

Asp Glu Xaa Xaa Gly Val Xaa Phe Asn Asp Xaa Thr
            20                  25

<210> SEQ ID NO 2
<211> LENGTH: 31
<212> TYPE: PRT
<213> ORGANISM: Mus musculus
<220> FEATURE:
<221> NAME/KEY: DOMAIN
<222> LOCATION: (410)...(440)
<223> OTHER INFORMATION: Plk polo box protein

<400> SEQUENCE: 2

Trp Val Ser Lys Trp Val Asp Tyr Ser Asp Lys Tyr Gly Leu Gly Tyr
1               5                   10                  15
```

```
Gln Leu Cys Asp Asn Ser Val Gly Val Leu Phe Asn Asp Ser Thr
            20                  25                  30

<210> SEQ ID NO 3
<211> LENGTH: 30
<212> TYPE: PRT
<213> ORGANISM: Saccharomyces cerevisiae
<220> FEATURE:
<221> NAME/KEY: DOMAIN
<222> LOCATION: (514)...(543)
<223> OTHER INFORMATION: CDC5 polo box

<400> SEQUENCE: 3

Val Thr Lys Trp Val Asp Tyr Ser Asn Lys His Gly Phe Ser Tyr Gln
1               5                   10                  15

Leu Ser Thr Glu Asp Ile Gly Val Leu Phe Asn Asn Gly Thr
            20                  25                  30

<210> SEQ ID NO 4
<211> LENGTH: 26
<212> TYPE: DNA
<213> ORGANISM: PCR Primer
<220> FEATURE:

<400> SEQUENCE: 4
tccaaaatat agaacgaata aatatc                                              26

<210> SEQ ID NO 5
<211> LENGTH: 28
<212> TYPE: DNA
<213> ORGANISM: PCR Primer
<220> FEATURE:

<400> SEQUENCE: 5
aaacgctata tgagaactat tgaaaagg                                            28

<210> SEQ ID NO 6
<211> LENGTH: 28
<212> TYPE: PRT
<213> ORGANISM: Artificial Sequence
<220> FEATURE:
<221> NAME/KEY: VARIANT
<222> LOCATION: (573)...(600)
<223> OTHER INFORMATION: PB2 consensus of sequences from the polo
      kinase proteins of 4 organisms:  Saccharomyces
      cerevisiae; Schizosaccharomyces pombe; Drosophila
      melanogaster; Mus musculus.  The residues labeled
      "Xaa" do not share a consensus among these
<222> LOCATION: refer to
      the location of the consensus sequence in the
      Saccharomyces cerevisiae CDC5 polo kinase gene.
      Xaa=Any amino acid
<223> OTHER INFORMATION: Xaa = Any Amino Acid

<400> SEQUENCE: 6

Ser Xaa Xaa Pro Xaa Ser Leu Xaa Xaa Lys Xaa Xaa Leu Leu Xaa Xaa
1               5                   10                  15

Phe Xaa Xaa Tyr Met Xaa Xaa Xaa Leu Xaa Lys Ala
            20                  25

<210> SEQ ID NO 7
<211> LENGTH: 30
<212> TYPE: PRT
<213> ORGANISM: Artificial Sequence
<220> FEATURE:
<221> NAME/KEY: VARIANT
<222> LOCATION: (615)...(643)
```

```
<223> OTHER INFORMATION: PB3 consensus of polo box sequences from
      the polo kinase proteins of 4 organisms:  Saccharomyces
      cerevisiae; Schizosaccharomyces pombe; Drosophila
      melanogaster; Mus musculus.  The residues labeled
      "Xaa" do not share a consensus among these
<222> LOCATION: refer to
      the location of the consensus sequence in the
      Saccharomyces cerevisiae polo gene.
      Xaa=Any amino acid
<223> OTHER INFORMATION: Xaa = Any Amino Acid

<400> SEQUENCE: 7

Leu Xaa Xaa Xaa Xaa Arg Thr Xaa Xaa Ala Xaa Xaa Xaa Xaa Leu Ser
 1               5                  10                  15

Asn Gly Xaa Xaa Gln Xaa Asn Xaa Phe Xaa Asp His Xaa Lys
            20                  25                  30

<210> SEQ ID NO 8
<211> LENGTH: 27
<212> TYPE: PRT
<213> ORGANISM: Mus musculus
<220> FEATURE:
<221> NAME/KEY: VARIANT
<222> LOCATION: (207)...(223)
<223> OTHER INFORMATION: Mek1

<400> SEQUENCE: 8

Cys Asp Phe Gly Val Ser Gly Gln Leu Ile Asp Ser Met Ala Asn Ser
 1               5                  10                  15

Phe Val Gly Thr Arg Ser Tyr Met Ser Pro Glu
            20                  25

<210> SEQ ID NO 9
<211> LENGTH: 29
<212> TYPE: PRT
<213> ORGANISM: Mus musculus
<220> FEATURE:
<221> NAME/KEY: VARIANT
<222> LOCATION: (193)...(221)
<223> OTHER INFORMATION: Plk

<400> SEQUENCE: 9

Gly Asp Phe Gly Leu Ala Thr Lys Val Glu Tyr Glu Gly Glu Arg Lys
 1               5                  10                  15

Lys Thr Leu Cys Gly Thr Pro Asn Tyr Ile Ala Pro Glu
            20                  25

<210> SEQ ID NO 10
<211> LENGTH: 29
<212> TYPE: PRT
<213> ORGANISM: Xenopus laevis
<220> FEATURE:
<221> NAME/KEY: DOMAIN
<222> LOCATION: (184)...(212)
<223> OTHER INFORMATION: Plx1

<400> SEQUENCE: 10

Gly Asp Phe Gly Leu Ala Thr Lys Val Glu Tyr Asp Gly Glu Arg Lys
 1               5                  10                  15

Lys Thr Leu Cys Gly Thr Pro Asn Tyr Ile Ala Pro Glu
            20                  25

<210> SEQ ID NO 11
<211> LENGTH: 29
<212> TYPE: PRT
<213> ORGANISM: Drosophila melanogaster
<220> FEATURE:
```

```
<221> NAME/KEY: DOMAIN
<222> LOCATION: (165)...(193)
<223> OTHER INFORMATION: Polo

<400> SEQUENCE: 11

Gly Asp Phe Gly Leu Ala Thr Arg Ile Glu Tyr Glu Gly Glu Arg Lys
 1               5                  10                  15

Lys Thr Leu Cys Gly Thr Ala Asn Tyr Ile Ala Pro Glu
            20                  25

<210> SEQ ID NO 12
<211> LENGTH: 29
<212> TYPE: PRT
<213> ORGANISM: Schizosaccharomyces pombe
<220> FEATURE:
<221> NAME/KEY: DOMAIN
<222> LOCATION: (180)...(208)
<223> OTHER INFORMATION: Plo1 polo box

<400> SEQUENCE: 12

Gly Asp Phe Gly Leu Ala Ala Leu Leu Met Asp Asp Glu Glu Arg Lys
 1               5                  10                  15

Met Thr Ile Cys Gly Thr Pro Asn Tyr Ile Ala Pro Glu
            20                  25

<210> SEQ ID NO 13
<211> LENGTH: 29
<212> TYPE: PRT
<213> ORGANISM: Saccharomyces cerevisiae
<220> FEATURE:
<221> NAME/KEY: DOMAIN
<222> LOCATION: (508)...(548)
<223> OTHER INFORMATION: CDC5 polo box

<400> SEQUENCE: 13

Gly Asp Phe Gly Leu Ala Ala Val Leu Ala Asn Glu Ser Glu Arg Lys
 1               5                  10                  15

Tyr Thr Ile Cys Gly Thr Pro Asn Tyr Ile Ala Pro Glu
            20                  25

<210> SEQ ID NO 14
<211> LENGTH: 29
<212> TYPE: PRT
<213> ORGANISM: Mus musculus
<220> FEATURE:
<221> NAME/KEY: DOMAIN
<222> LOCATION: (153)...(181)
<223> OTHER INFORMATION: Sak polo box

<400> SEQUENCE: 14

Ala Asp Phe Gly Leu Ala Thr Gln Leu Asn Met Pro His Glu Lys His
 1               5                  10                  15

Tyr Thr Leu Cys Gly Thr Pro Asn Tyr Ile Ser Pro Glu
            20                  25

<210> SEQ ID NO 15
<211> LENGTH: 29
<212> TYPE: PRT
<213> ORGANISM: Mus musculus
<220> FEATURE:
<221> NAME/KEY: DOMAIN
<222> LOCATION: (219)...(247)
<223> OTHER INFORMATION: Snk polo box

<400> SEQUENCE: 15

Gly Asp Phe Gly Leu Ala Ala Arg Leu Glu Pro Leu Glu His Arg Arg
```

```
1               5              10              15
Arg Thr Ile Cys Gly Thr Pro Asn Tyr Leu Ser Pro Glu
                20              25

<210> SEQ ID NO 16
<211> LENGTH: 29
<212> TYPE: PRT
<213> ORGANISM: Mus musculus
<220> FEATURE:
<221> NAME/KEY: DOMAIN
<222> LOCATION: (181)...(209)
<223> OTHER INFORMATION: Fnk polo box

<400> SEQUENCE: 16

Gly Asp Phe Gly Leu Ala Ala Arg Leu Glu Pro Pro Glu Gln Arg Lys
1               5                   10                  15

Lys Thr Ile Cys Gly Thr Pro Asn Tyr Val Ala Pro Glu
                20              25

<210> SEQ ID NO 17
<211> LENGTH: 29
<212> TYPE: PRT
<213> ORGANISM: Homo sapiens
<220> FEATURE:
<221> NAME/KEY: DOMAIN
<222> LOCATION: (163)...(191)
<223> OTHER INFORMATION: Prk polo box

<400> SEQUENCE: 17

Gly Asp Phe Gly Leu Ala Ala Arg Leu Glu Pro Pro Glu Gln Arg Lys
1               5                   10                  15

Lys Thr Ile Cys Gly Thr Pro Asn Tyr Val Ala Pro Glu
                20              25

<210> SEQ ID NO 18
<211> LENGTH: 41
<212> TYPE: PRT
<213> ORGANISM: Saccharomyces cerevisiae
<220> FEATURE:
<221> NAME/KEY: DOMAIN
<222> LOCATION: (508)...(548)
<223> OTHER INFORMATION: CDC5 protein C-terminal portion

<400> SEQUENCE: 18

Ile Lys His Pro Met Ile Val Thr Lys Trp Val Asp Tyr Ser Asn Lys
1               5                   10                  15

His Gly Phe Ser Tyr Gln Leu Ser Thr Glu Asp Ile Gly Val Leu Phe
                20              25                  30

Asn Asn Gly Thr Thr Val Leu Arg Leu
            35              40

<210> SEQ ID NO 19
<211> LENGTH: 41
<212> TYPE: PRT
<213> ORGANISM: Mus musculus
<220> FEATURE:
<221> NAME/KEY: DOMAIN
<222> LOCATION: (405)...(445)
<223> OTHER INFORMATION: Plk protein C-terminal portion

<400> SEQUENCE: 19

Cys Ile Pro Ile Phe Trp Val Ser Lys Trp Val Asp Tyr Ser Asp Lys
1               5                   10                  15

Tyr Gly Leu Gly Tyr Gln Leu Cys Asp Asn Ser Val Gly Val Leu Phe
                20              25                  30
```

-continued

```
Asn Asp Ser Thr Arg Leu Ile Leu Tyr
        35                  40

<210> SEQ ID NO 20
<211> LENGTH: 209
<212> TYPE: PRT
<213> ORGANISM: Mus musculus
<220> FEATURE:
<221> NAME/KEY: DOMAIN
<222> LOCATION: (395)...(603)
<223> OTHER INFORMATION: Plk protein C-terminal portion

<400> SEQUENCE: 20

Val Arg Gln Glu Glu Ala Glu Asp Pro Ala Cys Ile Pro Ile Phe Trp
 1               5                  10                  15

Val Ser Lys Trp Val Asp Tyr Ser Asp Lys Tyr Gly Leu Gly Tyr Gln
            20                  25                  30

Leu Cys Asp Asn Ser Val Gly Val Leu Phe Asn Asp Ser Thr Arg Leu
        35                  40                  45

Ile Leu Tyr Asn Asp Gly Asp Ser Leu Gln Tyr Ile Glu Arg Asp Gly
    50                  55                  60

Thr Glu Ser Tyr Leu Thr Val Ser Ser His Pro Asn Ser Leu Met Lys
65                  70                  75                  80

Lys Ile Thr Leu Leu Asn Tyr Phe Arg Asn Tyr Met Ser Glu His Leu
                85                  90                  95

Leu Lys Ala Gly Arg Asn Ile Thr Pro Arg Glu Gly Asp Glu Leu Ala
            100                 105                 110

Arg Leu Pro Tyr Leu Arg Thr Trp Phe Arg Thr Arg Ser Ala Ile Ile
        115                 120                 125

Leu His Leu Ser Asn Gly Thr Val Gln Ile Asn Phe Phe Gln Asp His
    130                 135                 140

Thr Lys Leu Ile Leu Cys Pro Leu Met Ala Ala Val Thr Tyr Ile Asn
145                 150                 155                 160

Glu Lys Arg Asp Phe Gln Thr Tyr Arg Leu Ser Leu Leu Glu Glu Tyr
                165                 170                 175

Gly Cys Cys Lys Glu Leu Ala Ser Arg Leu Arg Tyr Ala Arg Thr Met
            180                 185                 190

Val Asp Lys Leu Leu Ser Ser Arg Ser Ala Ser Asn Arg Leu Lys Ala
        195                 200                 205

Ser

<210> SEQ ID NO 21
<211> LENGTH: 201
<212> TYPE: PRT
<213> ORGANISM: Drosophila melanogaster
<220> FEATURE:
<221> NAME/KEY: DOMAIN
<222> LOCATION: (376)...(576)
<223> OTHER INFORMATION: Polo protein C-terminal portion

<400> SEQUENCE: 21

Asn Leu Gly Asp Glu Asn Thr Asp Pro Ala Ala Gln Pro Leu Phe Trp
 1               5                  10                  15

Ile Ser Lys Trp Val Asp Tyr Ser Asp Lys Tyr Gly Phe Gly Tyr Gln
            20                  25                  30

Leu Cys Asp Glu Gly Ile Gly Val Met Phe Asn Asp Thr Thr Lys Leu
        35                  40                  45

Ile Leu Leu Pro Asn Gln Ile Asn Val His Phe Ile Asp Lys Asp Gly
```

```
        50                  55                  60
Lys Glu Thr Tyr Met Thr Thr Asp Tyr Cys Lys Ser Leu Asp Lys
 65                  70                  75                  80

Lys Met Lys Leu Leu Ser Tyr Phe Lys Arg Tyr Met Ile Glu His Leu
                 85                  90                  95

Val Lys Ala Gly Ala Asn Asn Val Asn Ile Glu Ser Asp Gln Ile Ser
                100                 105                 110

Arg Met Pro His Leu His Ser Trp Phe Arg Thr Cys Ala Val Val
            115                 120                 125

Met His Leu Thr Asn Gly Ser Val Gln Leu Asn Phe Ser Asp His Met
        130                 135                 140

Lys Leu Ile Leu Cys Pro Arg Met Ser Ala Ile Thr Tyr Met Asp Gln
145                 150                 155                 160

Glu Lys Asn Phe Arg Thr Tyr Arg Phe Ser Thr Ile Val Glu Asn Gly
                165                 170                 175

Val Ser Lys Asp Leu Tyr Gln Lys Ile Arg Tyr Ala Gln Glu Lys Leu
            180                 185                 190

Arg Lys Met Leu Glu Lys Met Phe Thr
        195                 200

<210> SEQ ID NO 22
<211> LENGTH: 206
<212> TYPE: PRT
<213> ORGANISM: Schizosaccharomyces pombe
<220> FEATURE:
<221> NAME/KEY: DOMAIN
<222> LOCATION: (478)...(683)
<223> OTHER INFORMATION: Plo1 protein C-terminal portion

<400> SEQUENCE: 22

Thr His Ala Leu Thr Ser Glu Asp Ala Asp Ser Glu Pro Val Leu Phe
  1               5                  10                  15

Ile Thr Lys Trp Val Asp Tyr Ser Asn Lys Tyr Gly Leu Gly Tyr Gln
                 20                  25                  30

Leu Ser Asp Glu Ser Val Gly Val His Phe Asn Asp Asp Thr Ser Leu
             35                  40                  45

Leu Phe Ser Ala Asp Glu Glu Val Val Glu Tyr Ala Leu His Pro Lys
 50                  55                  60

Asp Thr Glu Ile Lys Pro Tyr Ile Tyr Pro Ala Ser Lys Val Pro Glu
 65                  70                  75                  80

Ser Ile Arg Ser Lys Leu Gln Leu Leu Lys His Phe Lys Ser Tyr Met
                 85                  90                  95

Gly Gln Asn Leu Ser Lys Ala Val Gln Asp Glu Ser Phe Glu Lys Pro
                100                 105                 110

Lys Asn Ser Thr Ser Asn Thr Met Leu Phe Met Gln His Tyr Leu Arg
            115                 120                 125

Thr Arg Gln Ala Ile Met Phe Arg Leu Ser Asn Gly Ile Phe Gln Phe
130                 135                 140

Asn Phe Leu Asp His Arg Lys Val Val Ile Ser Ser Thr Ala Arg Lys
145                 150                 155                 160

Ile Ile Val Leu Asp Lys Glu Arg Glu Arg Val Glu Leu Pro Leu Gln
                165                 170                 175

Glu Ala Ser Ala Phe Ser Glu Asp Leu Arg Ser Arg Leu Lys Tyr Ile
            180                 185                 190

Arg Glu Thr Leu Glu Ser Trp Ala Ser Lys Met Glu Val Ser
        195                 200                 205
```

```
<210> SEQ ID NO 23
<211> LENGTH: 207
<212> TYPE: PRT
<213> ORGANISM: Saccharomyces cerevisiae
<220> FEATURE:
<221> NAME/KEY: DOMAIN
<222> LOCATION: (499)...(705)
<223> OTHER INFORMATION: CDC5 protein C-terminal portion

<400> SEQUENCE: 23

Gly Leu Pro Lys Ser Arg Leu Pro Lys Ile Lys His Pro Met Ile Val
 1               5                  10                  15

Thr Lys Trp Val Asp Tyr Ser Asn Lys His Gly Phe Ser Tyr Gln Leu
            20                  25                  30

Ser Thr Glu Asp Ile Gly Val Leu Phe Asn Asn Gly Thr Thr Val Leu
        35                  40                  45

Arg Leu Ala Asp Ala Glu Glu Phe Trp Tyr Ile Ser Tyr Asp Asp Arg
    50                  55                  60

Glu Gly Trp Val Ala Ser His Tyr Leu Leu Ser Glu Lys Pro Arg Glu
65                  70                  75                  80

Leu Ser Arg His Leu Glu Val Val Asp Phe Phe Ala Lys Tyr Met Lys
                85                  90                  95

Ala Asn Leu Ser Arg Val Ser Thr Phe Gly Arg Glu Glu Tyr His Lys
            100                 105                 110

Asp Asp Val Phe Leu Arg Arg Tyr Thr Arg Tyr Lys Pro Phe Val Met
        115                 120                 125

Phe Glu Leu Ser Asp Gly Thr Phe Gln Phe Asn Phe Lys Asp His His
    130                 135                 140

Lys Met Ala Ile Ser Asp Gly Gly Lys Leu Val Thr Tyr Ile Ser Pro
145                 150                 155                 160

Ser His Glu Ser Thr Thr Tyr Pro Leu Val Glu Val Leu Lys Tyr Gly
                165                 170                 175

Glu Ile Pro Gly Tyr Pro Glu Ser Asn Phe Arg Glu Lys Leu Thr Leu
            180                 185                 190

Ile Lys Glu Gly Leu Lys Gln Lys Ser Thr Ile Val Thr Val Asp
        195                 200                 205

<210> SEQ ID NO 24
<211> LENGTH: 583
<212> TYPE: PRT
<213> ORGANISM: Mus musculus
<220> FEATURE:
<221> NAME/KEY: CHAIN
<222> LOCATION: (1)...(583)
<223> OTHER INFORMATION: GRASP65 protein

<400> SEQUENCE: 24

Met Gly Leu Gly Ala Ser Ser Glu Gln Pro Ala Gly Glu Gly Phe
 1               5                  10                  15

His Leu His Gly Val Gln Glu Asn Ser Pro Ala Gln Gln Ala Gly Leu
            20                  25                  30

Glu Pro Tyr Phe Asp Phe Ile Ile Thr Ile Gly His Ser Arg Leu Asn
        35                  40                  45

Lys Glu Asn Asp Thr Leu Lys Ala Leu Leu Lys Ala Asn Val Glu Lys
    50                  55                  60

Pro Val Lys Leu Glu Val Phe Asn Met Lys Thr Met Arg Val Arg Glu
65                  70                  75                  80
```

-continued

```
Val Glu Val Val Pro Ser Asn Met Trp Gly Gln Gly Leu Leu Gly
                 85                  90                  95

Ala Ser Val Arg Phe Cys Ser Phe Arg Arg Ala Ser Glu His Val Trp
            100                 105                 110

His Val Leu Asp Val Glu Pro Ser Pro Ala Ala Leu Ala Gly Leu
        115                 120                 125

Arg Pro Tyr Thr Asp Tyr Ile Val Gly Ser Asp Gln Ile Leu Gln Glu
    130                 135                 140

Ser Glu Asp Phe Phe Thr Leu Ile Glu Ser His Glu Gly Lys Pro Leu
145                 150                 155                 160

Lys Leu Met Val Tyr Asn Ser Glu Ser Asp Ser Cys Arg Glu Val Thr
                165                 170                 175

Val Thr Pro Asn Ala Ala Trp Gly Glu Gly Ser Leu Gly Cys Gly
            180                 185                 190

Ile Gly Tyr Gly Tyr Leu His Arg Ile Pro Thr Gln Pro Ser Ser Gln
        195                 200                 205

Tyr Lys Lys Pro Pro Ser Ala Ser Ser Pro Gly Thr Pro Ala Lys Thr
    210                 215                 220

Pro Gln Pro Asn Ala Phe Pro Leu Gly Ala Pro Pro Trp Pro Ile
225                 230                 235                 240

Pro Gln Asp Ser Ser Gly Pro Glu Leu Gly Ser Arg Gln Ser Asp Tyr
                245                 250                 255

Met Glu Ala Leu Pro Gln Val Pro Gly Gly Phe Met Glu Gln Leu
            260                 265                 270

Pro Gly Pro Gly Ser Pro Gly His Gly Thr Ala Asp Tyr Gly Gly Cys
        275                 280                 285

Leu His Ser Met Glu Ile Pro Leu Gln Pro Pro Pro Val Gln Arg
    290                 295                 300

Val Met Asp Pro Gly Phe Leu Asp Val Ser Gly Met Ser Leu Leu Asp
305                 310                 315                 320

Ser Asn Asn Thr Ser Val Cys Pro Ser Leu Ser Ser Ser Leu Leu
                325                 330                 335

Thr Pro Thr Ala Val Ser Ala Leu Gly Pro Glu Asp Ile Gly Ser Ser
            340                 345                 350

Thr Ser Ser His Glu Arg Gly Gly Glu Ala Thr Trp Ser Gly Ser Glu
        355                 360                 365

Phe Glu Ile Ser Phe Pro Asp Ser Pro Gly Ser Gln Ala Gln Val Asp
    370                 375                 380

His Leu Pro Arg Leu Thr Leu Pro Asp Gly Leu Thr Ser Ala Ala Ser
385                 390                 395                 400

Pro Glu Gln Gly Leu Ser Ala Glu Leu Leu Glu Ala Gln Thr Glu Glu
                405                 410                 415

Pro His Thr Arg Ser Ala Cys Ile Ala Trp His Lys Leu Arg Gly His
            420                 425                 430

Pro Ala Asn Ser Arg Leu Pro His Ile Gln Ser Leu Gly Cys Val Lys
        435                 440                 445

Ala Pro Gly Asp Ile Trp Cys Ser Leu Ala Val Tyr Leu Ser Ser Cys
    450                 455                 460

Ser Leu Tyr Arg Gly Met Gly Phe Ala Thr Val His Met Tyr Ser Trp
465                 470                 475                 480

Ile Glu Arg Asn Arg Thr Leu Glu Gln Cys Pro Ala Ser Ile Glu Ala
                485                 490                 495

Gly Asp Gly Ser Asn Val Ser Val Lys His Trp His Leu Pro Gly Arg
```

-continued

```
            500                 505                 510
Glu Arg Leu Gln Ala Arg His Asn Val His Met Lys Met Gly Trp Gly
            515                 520                 525

Thr Arg Gly Cys Val His Lys Arg Pro His Trp Tyr Arg Gly Ala Pro
        530                 535                 540

Arg Ile Pro Met Pro Phe Leu Ile Leu Ile Leu Thr Leu Asp Glu Arg
545                 550                 555                 560

Ser Ser Ile Leu Gly His Leu Ile Ser Arg Met Glu Asp Ser Gly Pro
                565                 570                 575

Phe Arg Gly Thr Cys Leu Cys
            580

<210> SEQ ID NO 25
<211> LENGTH: 541
<212> TYPE: PRT
<213> ORGANISM: Mus musculus
<220> FEATURE:
<221> NAME/KEY: DOMAIN
<222> LOCATION: (1)...(541)
<223> OTHER INFORMATION: CCT-epsilon protein

<400> SEQUENCE: 25

Met Ala Ser Val Gly Thr Leu Ala Phe Asp Glu Tyr Gly Arg Pro Phe
1               5                   10                  15

Leu Ile Ile Lys Asp Gln Asp Arg Lys Ser Arg Leu Met Gly Leu Glu
            20                  25                  30

Ala Leu Lys Ser His Ile Met Ala Ala Lys Ala Val Ala Asn Thr Met
        35                  40                  45

Arg Thr Ser Leu Gly Pro Asn Gly Leu Asp Lys Met Met Val Asp Lys
    50                  55                  60

Asp Gly Asp Val Thr Ile Thr Asn Asp Gly Ala Thr Ile Leu Ser Met
65                  70                  75                  80

Met Asp Val Asp His Gln Ile Ala Lys Leu Met Val Glu Leu Ser Lys
                85                  90                  95

Ser Gln Asp Asp Glu Ile Gly Asp Gly Thr Thr Gly Val Val Val Leu
            100                 105                 110

Ala Gly Ala Leu Leu Glu Glu Ala Glu Gln Leu Leu Asp Arg Gly Ile
        115                 120                 125

His Pro Ile Arg Ile Ala Asp Gly Tyr Glu Gln Ala Ala Arg Ile Ala
    130                 135                 140

Ile Gln His Leu Asp Lys Ile Ser Asp Lys Val Leu Val Asp Ile Asn
145                 150                 155                 160

Asn Pro Glu Pro Leu Ile Gln Thr Ala Lys Thr Thr Leu Gly Ser Lys
                165                 170                 175

Val Ile Asn Ser Cys His Arg Gln Met Ala Glu Ile Ala Val Asn Ala
            180                 185                 190

Val Leu Thr Val Ala Asp Met Glu Arg Arg Asp Val Asp Phe Glu Leu
        195                 200                 205

Ile Lys Val Glu Gly Lys Val Gly Gly Arg Leu Glu Asp Thr Lys Leu
    210                 215                 220

Ile Lys Gly Val Ile Val Asp Lys Asp Phe Ser His Pro Gln Met Pro
225                 230                 235                 240

Lys Lys Val Val Asp Ala Lys Ile Ala Ile Leu Thr Cys Pro Phe Glu
                245                 250                 255

Pro Pro Lys Pro Lys Thr Lys His Lys Leu Asp Val Met Ser Val Glu
            260                 265                 270
```

```
Asp Tyr Lys Ala Leu Gln Lys Tyr Glu Lys Glu Lys Phe Glu Glu Met
            275                 280                 285
Ile Lys Gln Ile Lys Glu Thr Gly Ala Asn Leu Ala Ile Cys Gln Trp
        290                 295                 300
Gly Phe Asp Asp Glu Ala Asn His Leu Leu Gln Asn Gly Leu Pro
305                 310                 315                 320
Ala Val Arg Trp Val Gly Pro Glu Ile Glu Leu Ile Ala Ile Ala
                325                 330                 335
Thr Gly Gly Arg Ile Val Pro Arg Phe Ser Glu Leu Thr Ser Glu Lys
            340                 345                 350
Leu Gly Phe Ala Gly Val Val Gln Glu Ile Ser Phe Gly Thr Thr Lys
            355                 360                 365
Asp Lys Met Leu Val Ile Glu Lys Cys Lys Asn Ser Arg Ala Val Thr
    370                 375                 380
Ile Phe Ile Arg Gly Gly Asn Lys Met Ile Ile Glu Glu Ala Lys Arg
385                 390                 395                 400
Ser Leu His Asp Ala Leu Cys Val Ile Arg Asn Leu Ile Arg Asp Asn
                405                 410                 415
Arg Val Val Tyr Gly Gly Ala Ala Glu Ile Ser Cys Ala Leu Ala
                420                 425                 430
Val Ser Gln Glu Ala Asp Lys Cys Pro Thr Leu Glu Gln Tyr Ala Met
    435                 440                 445
Arg Ala Phe Ala Asp Ala Leu Glu Val Ile Pro Met Ala Leu Ser Glu
    450                 455                 460
Asn Ser Gly Met Asn Pro Ile Gln Thr Met Thr Glu Val Arg Ala Arg
465                 470                 475                 480
Gln Val Lys Glu Ser Asn Pro Ala Leu Gly Ile Asp Cys Leu His Lys
                485                 490                 495
Gly Ser Asn Asp Met Gln Tyr Gln His Val Ile Glu Thr Leu Ile Gly
                500                 505                 510
Lys Lys Gln Gln Ile Ser Leu Ala Thr Gln Met Val Arg Met Ile Leu
            515                 520                 525
Lys Ile Asp Asp Ile Arg Lys Pro Gly Glu Ser Glu Glu
    530                 535                 540

<210> SEQ ID NO 26
<211> LENGTH: 603
<212> TYPE: PRT
<213> ORGANISM: Mus musculus
<220> FEATURE:
<221> NAME/KEY: DOMAIN
<222> LOCATION: (1)...(603)
<223> OTHER INFORMATION: Plk protein

<400> SEQUENCE: 26

Met Asn Ala Ala Ala Lys Ala Gly Lys Leu Ala Arg Ala Pro Ala Asp
1               5                   10                  15
Leu Gly Lys Gly Gly Val Pro Gly Asp Ala Val Pro Gly Ala Pro Val
            20                  25                  30
Ala Ala Pro Leu Ala Lys Glu Ile Pro Glu Val Leu Val Asp Pro Arg
        35                  40                  45
Ser Arg Arg Gln Tyr Val Arg Gly Arg Phe Leu Gly Lys Gly Gly Phe
    50                  55                  60
Ala Lys Cys Phe Glu Ile Ser Asp Ala Asp Thr Lys Glu Val Phe Ala
65                  70                  75                  80
```

-continued

```
Gly Lys Ile Val Pro Lys Ser Leu Leu Lys Pro His Gln Lys Glu
                85                  90                  95
Lys Met Ser Met Glu Ile Ser Ile His Arg Ser Leu Ala His Gln His
            100                 105                 110
Val Val Gly Phe His Asp Phe Glu Asp Ser Asp Phe Val Phe Val
        115                 120                 125
Val Leu Glu Leu Cys Arg Arg Ser Leu Leu Glu Leu His Lys Arg
    130                 135                 140
Arg Lys Ala Leu Thr Glu Pro Glu Ala Arg Tyr Tyr Leu Arg Gln Ile
145                 150                 155                 160
Val Leu Gly Cys Gln Tyr Leu His Arg Asn Gln Val Ile His Arg Asp
                165                 170                 175
Leu Lys Leu Gly Asn Leu Phe Leu Asn Glu Asp Leu Glu Val Lys Ile
            180                 185                 190
Gly Asp Phe Gly Leu Ala Thr Lys Val Glu Tyr Glu Gly Glu Arg Lys
        195                 200                 205
Lys Thr Leu Cys Gly Thr Pro Asn Tyr Ile Ala Pro Glu Val Leu Ser
    210                 215                 220
Lys Lys Gly His Ser Phe Glu Val Asp Val Trp Ser Ile Gly Cys Ile
225                 230                 235                 240
Met Tyr Thr Leu Leu Val Gly Lys Pro Pro Phe Glu Thr Ser Cys Leu
                245                 250                 255
Lys Glu Thr Tyr Leu Arg Ile Lys Lys Asn Glu Tyr Ser Ile Pro Lys
            260                 265                 270
His Ile Asn Pro Val Ala Ala Ser Leu Ile Gln Lys Met Leu Gln Thr
        275                 280                 285
Asp Pro Thr Ala Arg Pro Thr Ile His Glu Leu Leu Asn Asp Glu Phe
    290                 295                 300
Phe Thr Ser Gly Tyr Ile Pro Ala Arg Leu Pro Ile Thr Cys Leu Thr
305                 310                 315                 320
Ile Pro Pro Arg Phe Ser Ile Ala Pro Ser Ser Leu Asp Pro Ser Ser
                325                 330                 335
Arg Lys Pro Leu Lys Val Leu Asn Lys Gly Val Glu Asn Pro Leu Pro
            340                 345                 350
Asp Arg Pro Arg Glu Lys Glu Glu Pro Val Val Arg Glu Thr Asn Glu
        355                 360                 365
Ala Ile Glu Cys His Leu Ser Asp Leu Leu Gln Gln Leu Thr Ser Val
    370                 375                 380
Asn Ala Ser Lys Pro Ser Glu Arg Gly Leu Val Arg Gln Glu Glu Ala
385                 390                 395                 400
Glu Asp Pro Ala Cys Ile Pro Ile Phe Trp Val Ser Lys Trp Val Asp
                405                 410                 415
Tyr Ser Asp Lys Tyr Gly Leu Gly Tyr Gln Leu Cys Asp Asn Ser Val
            420                 425                 430
Gly Val Leu Phe Asn Asp Ser Thr Arg Leu Ile Leu Tyr Asn Asp Gly
        435                 440                 445
Asp Ser Leu Gln Tyr Ile Glu Arg Asp Gly Thr Glu Ser Tyr Leu Thr
    450                 455                 460
Val Ser Ser His Pro Asn Ser Leu Met Lys Lys Ile Thr Leu Leu Asn
465                 470                 475                 480
Tyr Phe Arg Asn Tyr Met Ser Glu His Leu Leu Lys Ala Gly Ala Asn
                485                 490                 495
Ile Thr Pro Arg Glu Gly Asp Glu Leu Ala Arg Leu Pro Tyr Leu Arg
```

```
                    500                 505                 510
Thr Trp Phe Arg Thr Arg Ser Ala Ile Ile Leu His Leu Ser Asn Gly
            515                 520                 525

Thr Val Gln Ile Asn Phe Phe Gln Asp His Thr Lys Leu Ile Leu Cys
        530                 535                 540

Pro Leu Met Ala Ala Val Thr Tyr Ile Asn Glu Lys Arg Asp Phe Gln
545                 550                 555                 560

Thr Tyr Arg Leu Ser Leu Leu Glu Glu Tyr Gly Cys Cys Lys Glu Leu
                565                 570                 575

Ala Ser Arg Leu Arg Tyr Ala Arg Thr Met Val Asp Lys Leu Leu Ser
            580                 585                 590

Ser Arg Ser Ala Ser Asn Arg Leu Lys Ala Ser
        595                 600

<210> SEQ ID NO 27
<211> LENGTH: 172
<212> TYPE: PRT
<213> ORGANISM: Homo sapiens
<220> FEATURE:
<221> NAME/KEY: DOMAIN
<222> LOCATION: (1)...(172)
<223> OTHER INFORMATION: TCTP/23 protein

<400> SEQUENCE: 27

Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
                20                  25                  30

Gly Lys Met Val Ser Arg Thr Glu Gly Asn Ile Asp Asp Ser Leu Ile
            35                  40                  45

Gly Gly Asn Ala Ser Ala Glu Gly Pro Glu Gly Glu Gly Thr Glu Ser
        50                  55                  60

Thr Val Ile Thr Gly Val Asp Ile Val Met Asn His Leu Gly Glu
65                  70                  75                  80

Thr Ser Phe Thr Lys Glu Ala Tyr Lys Lys Tyr Ile Lys Asp Tyr Met
                85                  90                  95

Lys Ser Ile Lys Gly Lys Leu Glu Glu Gly Arg Pro Glu Arg Val Lys
            100                 105                 110

Pro Phe Met Thr Gly Ala Ala Glu Gly Ile Lys His Ile Leu Ala Asn
        115                 120                 125

Phe Lys Asn Tyr Gly Phe Phe Ile Gly Glu Asn Met Asn Pro Asp Gly
    130                 135                 140

Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys
                165                 170
```

What is claimed is:

1. A method of inhibiting growth of an isolated population of cells by inhibiting a cell polo kinase, comprising: delivering to the population of cells a polo kinase inhibitor, wherein the inhibitor amino acid sequence consists of an amino acid sequence derived from a carboxy terminal domain of the polo kinase, such carboxy terminal domain excluding the polo kinase catalytic domain, wherein the amino acid sequence of the inhibitor comprises at least one of the sequences selected from the group consisting of PB1, PB2, and PB3 as set forth in SEQ ID NOs: 1, 6, and 7, respectively.

2. A method according to claim 1, wherein the inhibitor is an isolated peptide obtained by randomly mutagenizing a DNA sequence encoding the amino acid sequence of the polo kinase carboxy terminal domain.

3. A method according to claim 1, wherein the population of cells comprises cancer cells.

4. A method according to claim 1, wherein the inhibitor amino acid sequence is obtained from the amino acid sequence of a polo kinase of an unwanted population of cells isolated from an infected subject.

5. A method according to claim 1, wherein the inhibitor is delivered in an effective dose in a pharmaceutically acceptable carrier.

6. A method according to claim 2, wherein a nucleic acid sequence encoding the inhibitor is obtained by mutagenizing a subcloned nucleic acid sequence from a gene encoding a polo kinase, and isolating a genetically engineered peptide having increased binding affinity for a polo kinase.

7. A method according to claim 3, wherein the cancer is selected from the group consisting of a cancer of a lung, a breast, a uterus, an ovary, a cervix, an epithelium, a brain, a retina, a prostate, and a throat.

8. A method according to claim 4, wherein the cells are fungal cells.

9. A method according to claim 8, wherein the fungal cells are selected from the group of fungi consisting, of Candida, Lichen, Trichophyton, Epidermophyton, and Microsporum.

* * * * *